(12) United States Patent
Miethke et al.

(10) Patent No.: US 7,785,268 B2
(45) Date of Patent: Aug. 31, 2010

(54) IMPLANTABLE DEVICE FOR RECORDING INTRACRANIAL PRESSURES

(75) Inventors: Christoph Miethke, Potsdam (DE); Theodor Lutze, Balgheim (DE); Dirk Schauer, Berlin (DE)

(73) Assignees: Aesculap AG, Tuttlingen (DE); Christoph Miethke GmbH & Co. KG, Potsdam (DE)

( * ) Notice: Subject to any disclaimer, the term of this patent is extended or adjusted under 35 U.S.C. 154(b) by 131 days.

(21) Appl. No.: 11/978,183

(22) Filed: Oct. 25, 2007

(65) Prior Publication Data

US 2008/0139959 A1    Jun. 12, 2008

Related U.S. Application Data

(63) Continuation of application No. PCT/EP2006/003904, filed on Apr. 27, 2006.

(30) Foreign Application Priority Data

Apr. 30, 2005    (DE)    ........................ 10 2005 020 569

(51) Int. Cl.
*A61B 5/00*    (2006.01)
(52) U.S. Cl. ........................................ 600/561
(58) Field of Classification Search .................. 600/561
See application file for complete search history.

(56) References Cited

U.S. PATENT DOCUMENTS

| | | | |
|---|---|---|---|
| 3,946,724 A | | 3/1976 | La Balme |
| 4,127,110 A | * | 11/1978 | Bullara .................. 600/561 |
| 4,186,749 A | | 2/1980 | Fryer |
| 4,676,255 A | | 6/1987 | Cosman |
| 4,686,764 A | * | 8/1987 | Adams et al. .............. 29/592.1 |
| 4,738,267 A | | 4/1988 | Lazorthes et al. |
| 5,257,630 A | | 11/1993 | Broitman et al. |
| 5,461,922 A | * | 10/1995 | Koen ......................... 73/756 |
| 5,951,487 A | | 9/1999 | Brehmeier-Flick et al. |
| 6,083,174 A | | 7/2000 | Brehmeier-Flick et al. |
| 6,113,553 A | | 9/2000 | Chubbuck |
| 6,582,365 B1 | * | 6/2003 | Hines et al. ................. 600/300 |
| 6,673,022 B1 | | 1/2004 | Bobo et al. |

(Continued)

FOREIGN PATENT DOCUMENTS

DE    196 38 813    3/1998

(Continued)

OTHER PUBLICATIONS

Parker, "McGraw-Hill Dictionary of Scientific and Technical Terms Fifth Edition" p. 1578, 1994.*

*Primary Examiner*—Max Hindenburg
*Assistant Examiner*—Michael C Stout
(74) *Attorney, Agent, or Firm*—Lipsitz & McAllister, LLC

(57) ABSTRACT

To assure, in the case of an implantable device for determining intracranial pressures, the biocompatibility of the implant in the long term, wherein a pressure measuring device is used, which is operatively connected to a sensor for a telemetric measured value transfer, it is proposed that the pressure measuring device is a microchip, that the microchip is located in a rigid housing, and that the pressure transfer from the outside inwards occurs through a very thin biocompatible membrane, the pressure-dependent movement of which acts on the pressure measuring device via a transfer medium.

45 Claims, 38 Drawing Sheets

U.S. PATENT DOCUMENTS

| | | | | |
|---|---|---|---|---|
| 7,548,775 | B2* | 6/2009 | Kipke et al. | 600/378 |
| 2002/0138114 | A1* | 9/2002 | Gramse | 607/37 |
| 2003/0216666 | A1* | 11/2003 | Ericson et al. | 600/561 |
| 2005/0288722 | A1* | 12/2005 | Eigler et al. | 607/9 |
| 2006/0116602 | A1* | 6/2006 | Alden | 600/561 |
| 2006/0189888 | A1* | 8/2006 | Hassler et al. | 600/561 |

FOREIGN PATENT DOCUMENTS

| | | |
|---|---|---|
| DE | 197 05 474 | 8/1998 |
| DE | 197 13 266 | 10/1998 |
| DE | 198 58 172 | 6/2000 |
| DE | 101 56 494 | 6/2003 |
| EP | 1 312 302 | 5/2003 |

* cited by examiner

IMPLANTABLE DEVICE FOR RECORDING INTRACRANIAL PRESSURES

This application is a continuation of International patent application no. PCT/EP2006/003904 filed on Apr. 27, 2006 and claims the benefit of German patent application no. 10 2005 020 569.0 filed Apr. 30, 2005, each of which is incorporated herein and made a part hereof by reference.

BACKGROUND OF THE INVENTION

The invention relates to an implantable device for determining intracranial pressures, wherein a pressure measuring device is used, which is operatively connected to a sensor for a telemetric measured value transfer.

The determination of intracranial pressure assumes an extremely important role in neurosurgical procedures. The most precise and simple minimally invasive measurement of intracranial pressure possible counts to this day as one of the aims of medical technology that has not been satisfactorily resolved.

It has been the object of numerous inventions to solve this problem. However, all the systems available hitherto have serious disadvantages, and to overcome these is the object of the invention presented here.

Invasive measurement methods have prevailed in clinical practice, in which a sensor is inserted into the body, wherein the signal is passed via a cable connection to an external device for display and evaluation of the measured value. This frequently occurs in combination with an artificial drainage pipe, through which brain fluid is to be drained out of the body. The very high risk of infection is critical with such systems. Long procedures can only be conducted by very expensive prophylaxis against infections and with multiple replacements of the pressure sensor. However, especially in the case of patients with hydrocephalus, it is the progress of the intracranial pressure in an out of clinic situation after implantation of an internal artificial drainage system that is of high diagnostic interest. Systems, which pass the measured signal through the intact skin or allow measurement through the skin, are suitable for such tasks.

Patent DE 196 38 813 C1 describes an implantable pressure sensor, which is connected to flexible foil strip conductors and is surrounded by a substrate in the region of the sensor element, which has a higher mechanical strength than the foil strip conductor and which is enveloped together with the sensor element into a flexible body. The structure should make a reliable and inexpensive measuring device possible, which does not, however, enable any reduction with respect to the risk of infection because of the necessary penetration of the skin. In association with the sensor technology, reference is made to patent U.S. Pat. No. 4,738,267, in which a plastic capsule with a membrane is used, to which a strain gauge is attached. The imbalance of the Wheatstone bridge is interpreted as the magnitude for the existing pressure. Such a sensor operates imprecisely and exhibits an unacceptably high drift behaviour. For this reason, it has not prevailed as implantable intracranial pressure sensor.

The same technique is also described for telemetric determination of intracorporeal pressures in patent application DE 197 05 474 as an application for a patent of addition to DE 196 38 813 C1. However, there are no indications given here as to how biocompatibility is to be assured. Such a sensor has so far not advanced to the commercial stage.

A likewise telemetric method for determining intracranial pressure is described in patent U.S. Pat. No. 6,113,553. The claims applied for here relate to measurement that is as drift-free and stable in the long term as possible with description of the electronic structure. A capacitive structure is used here, wherein the sensor is to be embedded in the bone of the patient. This is necessary because of the bulky structure of the sensor. The extent to which the actual properties of the sensor design meet the high requirements for intracranial pressure measurement with respect to accuracy and drift behaviour is not known, since such a sensor is not as yet commercially available and therefore could not be subjected to any independent tests.

A method for determining intracranial pressure without skin penetration is likewise described in patent U.S. Pat. No. 4,676,255 from 1987. The idea here was to use the principle of relaxed membranes. A sensor placed under the skin has its zero position as long as intracranially in relation to the surrounding area no positive or negative differential pressure is present. When the intracranial pressure rises or falls, the sensor moves out of the zero position. The precise pressure that is necessary to bring the sensor into the zero position again is now applied through the skin. The pressure necessary for this should then correspond to the intracranial pressure. This method has not been able to prevail clinically. Reasons for this are the variance of skin from patient to patient, the technically difficult and imperfect determination of the zero position and also the complicated generation of the necessary external pressure pad.

Substantially better possibilities are offered by telemetric approaches, in which an extremely small pressure sensor is inserted into the body, which is connected by means of cable likewise inserted into the body to a coil, by means of which, on the one hand, the sensor can be supplied with energy where required and, on the other hand, the measured signal can be transmitted to the outside to a receiver unit for further processing.

A method is described in patent DE 198 58 172 that determines the intracorporeal pressure directly by means of a sensor element using microsystems technology. This centres on the determination of the internal pressure of the eye. The implant should therefore be as small and light as possible. The coating of the sensor is of decisive importance when using this technology to determine intracranial pressure. Such a sensor is described in patent DE 101 56 494, wherein a metal layer as well as a biocompatible plastic layer is provided at least in sections to assure biocompatibility. Such a structure has considerable disadvantages. A coating of the sensor element of whatever type permits impairment of the measurement because of the penetration through this very layer, the properties of which can change over time. The layer can be damaged as a result of the actions of forces from the outside. A drift behaviour can also be problematic as a result of ageing, in particular of the plastic layers.

In order to ensure a homogeneous and secure transfer of the pressure prevailing around the sensor, a technique is described in patent EP 1 312 302 A2, in which a medium arranged around the sensor is surrounded by a flexible sheath. How the biocompatibility of the flexible sheath is to be assured is not described in the patent document. The favoured use of silicone oil in the application for optimum transfer of the existing pressure appears problematic taking into consideration the risk factors.

SUMMARY OF THE INVENTION

The object forming the basis of the invention is, with an implantable device of the above general type, to use a miniaturised chip to determine the absolute pressure so that the biocompatibility of the implant is also assured in the long term and also that a measurement can be performed that is as far as possible drift-free and highly precise.

This object is achieved according to the invention with an implantable device of the above-described type in that the pressure measuring device is a microchip, that the microchip is located in a rigid housing, and that the pressure transfer from the outside inwards occurs through a very thin biocompatible membrane, the pressure-dependent movement of which acts on the pressure measuring device via a transfer medium.

The pressure sensor, which is arranged on a microchip and integrated into this, is protected from the surrounding area in the best possible way because of the arrangement in a rigid housing that is hermetically closed, and the surrounding area is also protected from the discharge of dangerous substances. By using a very thin membrane, the pressure of the brain fluid can be transferred to the interior of the rigid housing, and in this interior the pressure-dependent movement of the membrane is transmitted to the pressure measuring device via a transfer medium, so that a reliable and very direct determination of pressure fluctuations of the surrounding brain fluid is possible.

In particular, difficulties with respect to the passivation of the electronically operating sensor are overcome, which in particular concern the reliability of the protection with respect to ageing or damage, the impairment of the pressure transfer through the applied protective layer and the incalculable drift resulting in material changes occurring over time after implantation.

In a first preferred embodiment, air or a special gas or a liquid is used as transfer medium, wherein this transfer medium fills a chamber inside the rigid housing.

When using a gas as filling medium of the chamber, the mode of operation of the device can be described simply and precisely using the ideal gas equation. FIG. 1 shows a cylindrical container, the floor and cylindrical side wall of which are designed to be very thick, while its cover is designed to be very thin-walled as a membrane. The following applies for constant temperature conditions $$p*V = \text{constant} \quad (1)$$

If the pressure outside the container changes, there results a displacement of the membrane that can be calculated and is determined by the volume VI in the container, the characteristic of the membrane and the value of the externally acting pressure change. FIG. 2 shows a possible displacement of such a membrane for the case of the external pressure rise, wherein because of the stresses occurring in the membrane as a result of the curvature, the pressures inside and outside the container can be different. However, for each membrane position there is a characteristic pressure situation in the container, which corresponds to an externally prevailing pressure. Therefore, conclusions can be drawn with respect to the external pressure by measuring the pressure in the container. The absolute movement of the membrane is not linear to the prevailing pressure difference. If one wishes to perform an indirect pressure measurement by the pressure measurement in a container, then the chamber should have a relaxed membrane for the most frequently occurring pressure, as shown in FIG. 1. The lower the instance of stresses in the membrane with external pressure fluctuations, the more precise the pressure transfer from the outside inwards and the more precise the measurement becomes. In the best case, the pressure to be measured does not reach any values, at which substantial stresses result in the membrane.

FIG. 3 shows the displacement for the case of the drop in the externally prevailing pressure. Depending on the characteristic and shape of the membrane, no change, or only a very slight change, in stress results within the membrane. The principle of the relaxed membranes applies, wherein, provided that the membrane does not absorb any stresses, the pressure adjusts to the same value on both sides of the membrane. This principle is known in the art and is frequently used. However, it was not hitherto known that this principle can be ideally used for measuring body pressures and also safely for long periods of time and drift-free also for miniaturized microchip sensors, which are produced on the basis of silicon and could convincingly demonstrate their efficiency in many technical applications.

In order to achieve as efficient and direct a pressure transfer as possible from the outside inwards, although the preferably metal membrane (made ideally of sheet titanium or a titanium foil) is comparatively rigid, the air volume available in the sensor should be as low as possible at ambient pressure. FIG. 1 shows a container filled with gas (air), the internal pressure of which corresponds exactly to the external pressure without the membrane being curved. FIG. 3 shows this same container, but now for a lower external pressure: the membrane is turned outwards. As a consequence the pressure in the container also drops. FIG. 4 shows a container, wherein the air volume is designed to be minimally small. However, since in this case the membrane is designed exactly as in FIG. 1 to FIG. 3, the theoretically displaceable air volume in the sensor, with which still no appreciable stresses result in the membrane, is precisely as large as in the cases with large container volume (FIG. 1 to FIG. 3). The membrane can now transfer the external pressure without any substantial membrane movement to the container chamber because of the very small internal air volume. Only a very small membrane displacement is necessary to create a pressure equilibrium for this container between inside and outside even with substantial changes in the external pressure. Because of the small size of the air chamber in the container according to FIG. 4, the representation applies for all three case, as shown and described in FIG. 1 to FIG. 3. The membrane displacement is scarcely visible. In the case of intracranial pressure measurement, pressure fluctuations of few cm water column are of therapeutic interest. The absolute values of these pressure fluctuations always lie in the range of atmospheric pressure fluctuations, i.e. approximately at 10 m water column +/−1 m water column. Sensors, which should be used in high mountains, for example, would therefore have to be designed differently accordingly. The more precisely the normal ambient pressure can be restricted in the individual case, the more precisely the pressure recorder can operate, since the relevant absolute pressure range can be restricted further. Measurements of the intracorporeal absolute pressure are then not possible or defective for pressure values lying outside the range.

To form an ideal pressure sensor for the measurement of intracranial pressure, only a little more air volume is used on the sensor side than is displaced by the membrane displacement in the case of a pressure gradient from the outside inwards to the amount of maximum 100 cm water column, preferably also only 50 cm water column. In this case, the space inside the sensor should be configured such that no obstacles formed by sensor components oppose the membrane movement. A rise in the pressure to be measured to the maximum permissible value leads to a membrane movement, which just does not yet allow any contact of the membrane with the actual sensor unit, and contact results with a further rise in pressure.

In particular for large pressure ranges embodiments are also provided, wherein a stress-free or low-stress displacement of the membrane does not exclusively result. Sensors may be considered here that can be used both with extremely low and extremely high pressure to be measured. In this case, the signal of the pressure recorder does not indicate a uniform progress. The sensor changes its characteristic as a function of the stress state in the membrane, which is dependent in turn on the prevailing pressure. Such sensors have an individual characteristic that enables them to associate an externally prevailing pressure with a measured pressure inside the sensor. The association can be achieved by recognition of the sensor by the external reader, which then knows the pressure value corresponding to the transmitted signal.

The gas used can be a gas from the group of noble gases, for example.

It is advantageous if, with the use of a gas as transfer medium, its gas volume is less than a cubic millimetre, preferably less than 0.1 cubic millimetre.

In a preferred embodiment, the housing interior is filled with a gas-displacing filler material except for the provided volume of gas or liquid.

In this case, this can be a plastic material, a ceramic material or a metal material, for example.

It is advantageous in particular if the filler material leaves a minimum-volume pressure chamber including supply duct free on the pressure-sensitive faces of the microchip, and if the filler material leaves a housing cavity as pressure chamber free below the membrane, and if the two pressure chambers are connected by a small-volume conduit.

In another embodiment, the transfer medium can have at least one mechanical transfer member which is movable by the membrane.

The transfer member can be held either on the microchip or on a support receiving the microchip, in another embodiment on the membrane.

In a first embodiment, the transfer member is a pressure foot. In another case, the transfer member is a spring, in particular a U-shaped leaf spring.

In this case, it is favourable if the spring is held on the housing or the support by means of holding elements.

In a further preferred exemplary embodiment, the transfer member has a clip, which is disposed on the housing or on a support receiving the microchip and which abuts against the microchip or the membrane respectively with a foot.

It is favourable if stop elements are provided, which restrict the movement of the mechanical transfer member.

The transfer medium can also be a highly viscous oil or a vulcanised or polymerised material. In particular, a cross-linked silicone may be considered as transfer medium in this case.

The microchip can be completely encapsulated with the vulcanised or polymerised material.

However, it is advantageous if the microchip is only covered or encapsulated with the vulcanised or polymerised material in the region of a pressure sensor, whereas the other regions are not covered with such a material.

The vulcanised or polymerised material can fill the entire cavity between the microchip and the membrane, but according to a preferred embodiment it can also be provided that the vulcanised or polymerised material only abuts against the membrane in the region of the pressure sensor, so that a pressure transfer occurs only in this region.

The vulcanised or polymerised material can also be arranged on the membrane, so that the membrane is covered with the vulcanised or polymerised material in a region located opposite the pressure sensor of the microchip and this material abuts against the microchip at least in the region of the pressure sensor.

It can also be advantageous here if the vulcanised or polymerised material abuts against the microchip only in the region of the pressure sensor, but the other regions of the microchip remain free.

The rigid housing can be made of any materials that are biocompatible. Particularly advantageous is the configuration made of ceramic, of a biocompatible plastic such as polyether ether ketone or polyether ketone ketone, for example, or the configuration as a metal housing, wherein the metal used is preferably titanium or a titanium alloy.

The membrane is preferably made of metal, in particular titanium or a titanium alloy.

It is advantageous here if the membrane has a thickness of less than 0.05 millimeters, preferably of less than 0.01 millimeters, and further preferred about 0.005 millimeters.

Depending on the embodiment, the membrane can have a flexible surface of between 1 mm$^2$ and 100 mm$^2$, in particular of about 4 mm$^2$.

It is favourable if the membrane is welded to the housing.

For example, it can be provided that the membrane is provided with a sheet metal frame and is welded with the frame to the housing.

In a special embodiment with a tubular housing the frame can be formed by a sleeve, which can be slid onto the tubular housing to close this.

This sleeve can be welded simultaneously with the membrane on the tubular housing along the outer edge of the sleeve, wherein a hole in the housing wall is closed precisely so that the membrane, and not the sleeve, comes to lie over the hole and is secured there.

In another preferred embodiment, it is provided that the membrane is configured in one piece with the housing. This results in maximum protection against leakage.

The membrane can have regions of different thickness. In particular it can be provided that the membrane is thicker in its edge regions than in its central region. As a result of this, a high strength is achieved in the transition region between the membrane and housing, which enables leakage in this region to be reliably prevented. In a preferred embodiment it is provided that besides at least one pressure sensor the microchip has at least one further sensor. This can be a temperature sensor, for example.

It is additionally favourable if, besides the pressure sensor and besides possibly further sensors, the microchip comprises an analog-to-digital converter, which converts the analog electrical signals of the sensors into digital signals. This assures that the signals from the sensor are transmitted in digital form to an evaluation unit outside the body, so that the susceptibility to interference is reduced quite considerably compared to the transmission of analog signals. The analog-to-digital converter can be integrated on the microchip as can the sensor and as can possibly other electronic function units, e.g. units for the unambiguous identification of the microchip or units, which prepare the digital signals for the transmission via a high-frequency carrier.

As a result of the integration of these functions in a microchip, it is possible to construct a device of very small design, so that this device can be placed at the desired location without difficulties.

In a particularly preferred embodiment it is provided that the microchip is connected to a power and signal transmission line, which connects to a data processing device outside the body or to a transmission coil. Power can thus be supplied externally to the microchip, no power storage means are necessary in the device, and as a result of this, on the one hand, the service life is increased and, on the other hand, the implantable device can be very small.

Still further electronic components in addition to the microchip can be arranged in the housing in all embodiments, e.g. diodes and capacitors to restrict power and buffer power. It is advantageous in this case if a support is arranged in the housing, to which both the microchip and these electronic components are attached and which also receives the connection leads between the microchip, the additional electronic components and the power and signal transmission line.

It is possible, in principle, to arrange the transmission coil in the rigid housing. However, in most cases it advantageous to arrange the power and signal transmission line outside the rigid housing, so that the rigid housing only encloses the microchip and the electronic units that are absolutely necessary thereon and can be of small design accordingly.

It is advantageous if all electrical and electronic components and other non-biocompatible components are housed in the housing, since these components are hermetically sealed relative to the surrounding area. In certain exemplary embodiments the transmission coil can be arranged outside the housing, if need be, and this can be configured to be biocompatible. For example, the coil can be made of gold, platinum or silver and be encased in an atoxic and biocompatible manner.

The power and signal transmission line is advantageously guided out of the rigid housing through a hermetically sealed bushing. This ensures that the interior of the housing is sealed absolutely tightly with respect to the exterior, and in spite of this power can be supplied to the microchip and the digital signals generated by the microchip can be transmitted to an evaluation unit. Such a hermetic bushing is naturally only necessary for the power transmission when the transmission coil is arranged inside the rigid housing, however if the transmission coil is arranged outside the rigid housing, both the power transmission line and the signal transmission line must be directed through such a bushing. These can be separate lines or can also be a common line.

It is favourable if a releasable coupling, in particular in the form of a plug contact, is arranged in the power and signal transmission line. In this case, it is generally provided that this plug contact is also hermetically sealed with respect to the surrounding area.

In other cases, the hermetic bushing in the housing is permanently connected to the power and signal transmission line, e.g. by soldering, welding, by conductive adhesive or crimping.

It is additionally advantageous if the rigid housing is partially provided with a plastic casing or a plastic covering, which, however, leaves at least the surface of the membrane free. Such a plastic casing or plastic covering additionally protects the housing, and the surrounding tissue is additionally protected as a result of this.

The intracranial pressure measurement can be conducted at different measurement sites in the brain, and different configurations result for the rigid housing in keeping with the different measurement sites.

In a first preferred embodiment it is provided that the rigid housing is tubular in configuration.

In the case of such a tubular housing a window, which is closed by the membrane, can be provided in the housing wall.

It is particularly favourable if the diameter of the housing lies to between 2 mm and 3.5 mm, in particular between 2.5 mm and 3 mm. Such a housing is particularly suitable for intraventricular pressure measurement, the outside diameter corresponds to a typical ventricle catheter normally used in hydrocephalus therapy.

In this case, the length of the housing can lie to between 10 mm and 30 mm, in particular about 20 mm. This is thus a very small housing, which can also be arranged in deeper regions of the brain without difficulty and then connects to the transmission coil or to the evaluation unit by means of the power and signal transmission line.

In this case, it is advantageous if the pressure sensor is arranged approximately in the centre of the longitudinal extent of the housing.

It is provided in another embodiment that the length of the tubular housing lies to between 80 mm and 120 mm, in particular about 100 mm. With such a configuration, the tubular housing extends from the measurement site as far as the outside of the cranium, so that a power and signal transmission line directed hermetically through the housing wall is not absolutely necessary.

With such a configuration it is advantageous if the microchip and the membrane are arranged at one end of the tubular housing and a transmission coil at the opposite end. This then preferably lies outside the cranial bone.

In another preferred configuration, the rigid housing can have a closed fluid chamber, which adjoins the membrane on the outside and is connected to a supply conduit for fluid. In the case of such a configuration, the pressure of the fluid in the closed fluid chamber is determined by the pressure sensor via the membrane. This can be brain fluid directly or can be measurement fluid, which is located in the closed fluid chamber and which is acted on by the pressure of the brain fluid in a different manner.

The fluid chamber can additionally have a drainage pipe for fluid. This is important in particular if brain fluid is directed through the fluid chamber and then removed from the brain chamber via the drainage pipe.

It is favourable with such a configuration if the rigid housing has the shape of a shallow can with an upper measurement chamber receiving the microchip and the transfer medium and a lower region forming the fluid chamber. Such a housing in the shape of a shallow can can be placed externally on the cranial bone, i.e. either over the drill hole in the cranial bone or directly next to this.

It is advantageous if the membrane divides the interior of the housing into the measurement chamber and the fluid chamber, as a result of which the membrane extends over a very large area and reacts appropriately sensitively to pressure changes of the fluid in the fluid chamber.

The supply conduit for the fluid can run substantially perpendicularly in relation to a lower boundary wall of the fluid chamber. This is advantageous particularly when the housing is placed directly on a drill hole in the cranial bone, the supply conduit then being able to pass through this drill hole.

For example, the supply conduit for the fluid enters the fluid chamber substantially centrally in relation to a lower boundary wall of the fluid chamber.

In another embodiment it is provided that the supply conduit for the fluid runs substantially parallel in relation to a lower boundary wall of the fluid chamber.

The drainage pipe for the brain fluid can also run parallel to the lower boundary wall. With such a configuration the housing can also be arranged next to the drill hole in the top of the cranium, the supply conduit then being guided through the drill hole and directed parallel to the cranial bone into the fluid chamber.

It is favourable if a non-return valve is arranged in the drainage pipe.

The drainage pipe can open into a reservoir, from which liquid can be backwashed, for example, in order clean the fluid conduits.

It is favourable if the supply conduit is connected to an extension tube, which is open at its end remote from the fluid chamber. Such an extension tube acts as a ventricle catheter and can direct brain fluid from the measurement region directly into the fluid chamber. With such an arrangement the intracranial pressure can be determined at the entry region of the extension tube.

In another embodiment it is provided that the supply conduit is connected to an extension tube, which is closed at its end remote from the fluid chamber by means of a flexible membrane. The extension tube and the fluid chamber are filled with a liquid or a gas and form a closed space, which acts as a pressure transfer medium between the membrane closing off the extension tube and the membrane closing off the measurement chamber.

The wall thickness of the rigid housing can lie between 0.3 mm and 2 mm, so that a deformation-resistant rigid housing is obtained.

To further increase this deformation resistance, it can be provided that the walls of the rigid housing are protected against deformation by reinforcement structures.

In a further preferred embodiment, the measurement chamber can be arranged in an insert, which can be inserted into the housing and closes this in the manner of a cover, wherein the insert carries a membrane, which separates the measurement chamber from the interior of the housing forming the fluid chamber. Therefore, the insert with the membrane and the separated measurement chamber form a separate structural part, which can be inserted into the housing and which as a result of the insertion closes off the housing and also separates the fluid chamber.

The membrane can be a metal foil, which is soldered or welded to the structural part receiving the measurement chamber. This is also possible when the membrane is not held on a separate insert, but on a part of the rigid housing itself.

A permanent and secure seal of the measurement chamber is obtained as a result of the soldering and welding.

According to a preferred embodiment it can be provided that the structural part receiving the measurement chamber has a planar rim, against which the membrane lies flat, that an annular abutment element is arranged opposite the planar rim on the side opposite the structural part, and that the membrane is soldered or welded both to the structural part and to the abutment element. The abutment element and the structural part thus receive the membrane between them in a sandwich-like arrangement and enable the membrane to be soldered or welded both to the structural part and to the abutment element, so that the connection point is also mechanically secured to the outside.

The structural part can be made of metal, preferably titanium or a titanium alloy.

The abutment element can likewise be made of metal, in particular titanium or a titanium alloy.

The membrane can also be made of metal, in particular titanium or a titanium alloy.

It is favourable in this case if the thickness of the membrane lies between $1/100$ mm and $5/100$ mm, preferably in the order of 2 to $3/100$ mm. The abutment element can preferably have a height of between $3/10$ and $8/10$ mm, in particular in the order of $5/10$ mm.

The combination of features described above is particularly advantageous, but the invention also relates to configurations, in which these features are utilised only individually or in which only a portion of these features is utilised in combination.

The invention additionally relates to a process for the production of a rigid housing with a membrane for use in an implantable device of the type described above. Such a process is characterised according to the invention in that a specific wall region of the otherwise rigid housing is weakened by a chemical etching process or electrolytic removal process to such an extent that it forms a flexible membrane.

Overall it can be provided that the thickness of the specific wall region is reduced by machining before the etching or removal process.

The thickness of the membrane can be selected to be equal over the entire membrane surface, but according to a preferred embodiment it is provided that the thickness of the specific wall region is selected to vary in thickness before the etching or removal process, so that after the etching or removal process a membrane is obtained that has different thicknesses in different regions.

In particular it can be provided that the thickness of the specific wall region is reduced to a lesser degree in the outer wall regions than in the central region.

A process for the production of a rigid housing with a membrane for an implantable device of the described type can also be characterised according to the invention in that a membrane is laid flat against a planar rim of a structural part receiving a measurement chamber, that on the side opposite the structural part an annular abutment element located opposite the rim is laid flat against the membrane, said membrane is clamped between the structural part and the abutment element, and then the structural part, the membrane and the annular abutment element are soldered or welded together.

In this case, it is advantageous if the membrane is allowed to project slightly beyond the contour of the structural part and/or the annular abutment element and the soldering or welding is conducted completely or partially on this projecting edge strip.

It is also possible here, particularly in the case of welding, to remove the piece of membrane projecting beyond the contour of the structural part and/or the annular abutment element during the welding process.

BRIEF DESCRIPTION OF THE DRAWINGS

The following description of preferred embodiments of the invention serves as more detailed explanation in association with the drawing.

DETAILED DESCRIPTION

Figure 1:
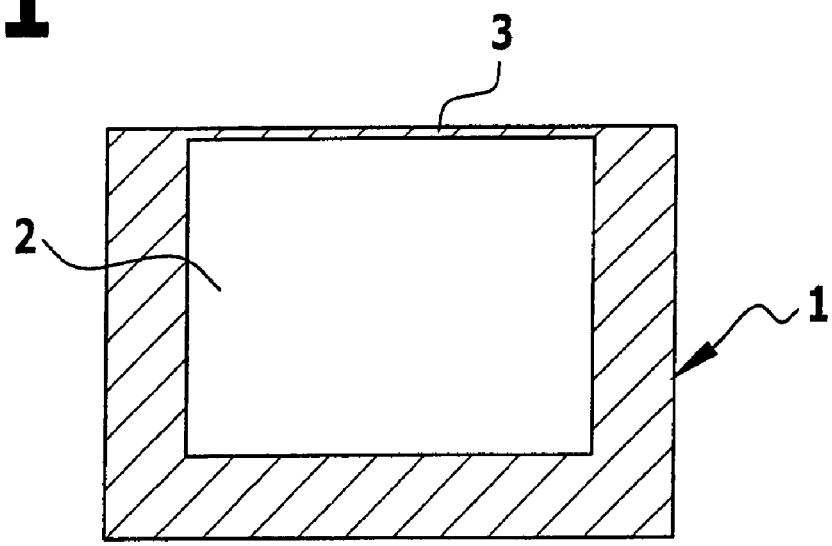
FIG. 1 is a schematic view of a rigid housing to receive a microchip provided with a pressure sensor and a thin flexible membrane closing off the housing on one side, in a neutral position.
Figure 2:
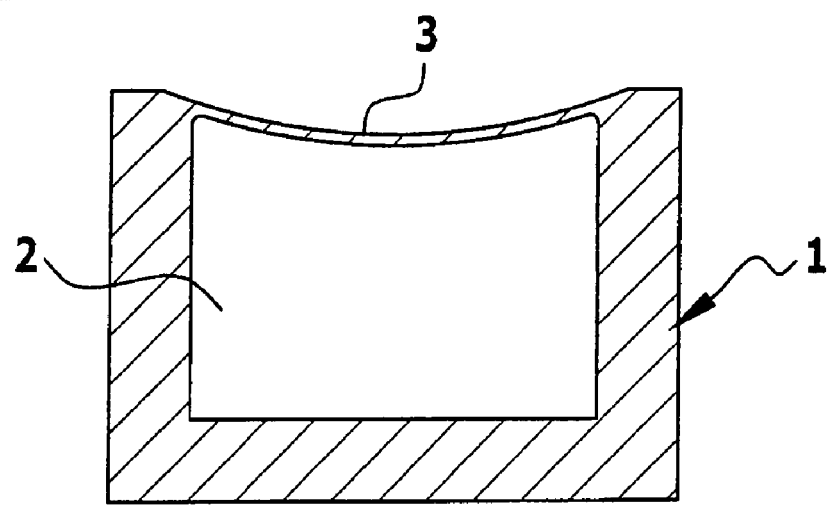
FIG. 2 is a view similar to FIG. 1 with the membrane in a pressed-in position.
Figure 3:
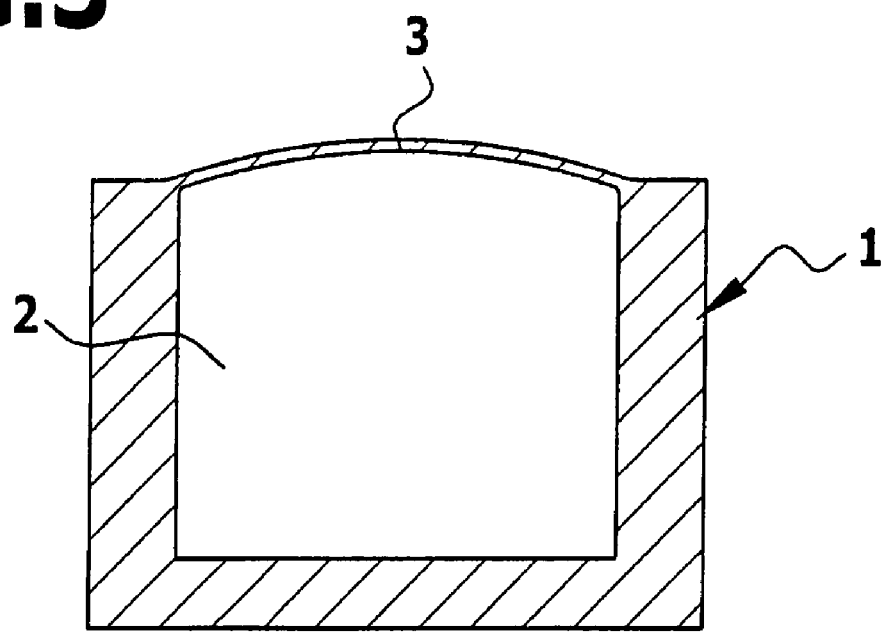
FIG. 3 is a view similar to FIG. 1 with the membrane in a pushed-out position.

As already explained, the implantable device for determining intracranial pressure comprises a rigid housing 1 with an interior 2, which is closed off to the outside by means of a flexible, preferably elastic membrane 3. The rigid housing is configured so that it is as free from deformation as possible at the occurring pressures. It can be made, for example, of ceramic, a biocompatible plastic (polyether ether ketone, polyether ketone ketone) or of metal (titanium, titanium alloy) and can additionally have an internal reinforcement structure, e.g. by supports passing through the interior or reinforcing ribs on the housing 1, which are not shown in the drawing.

The wall thickness of the housing lies between 0.3 millimeters and 2 millimeters, whereas the thickness of the membrane is considerably smaller, e.g. in the order of between 0.005 millimeters and 0.05 millimeters.

To produce the membrane, a single-piece housing can be worked from in particular, which is reduced in thickness in a specific wall region by a machining operation or in another way. A housing is then obtained that has very highly deformation-resistant walls, the wall thickness only being reduced in the region of the predetermined wall region by the mechanical premachining.

The wall in the predetermined wall region is then further reduced in thickness, i.e. by means of a chemical etching process or by an electrolytic removal process, until the desired thickness of the membrane is reached.

Figure 33A:
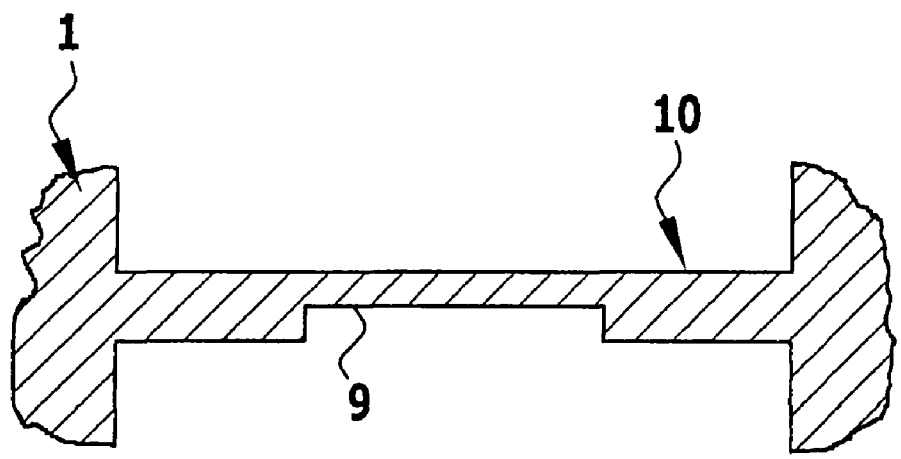
FIG. 33*a* is a schematic cross-sectional representation of a housing with a predetermined wall region of reduced thickness before an etching process for the production of a membrane.
Figure 33B:
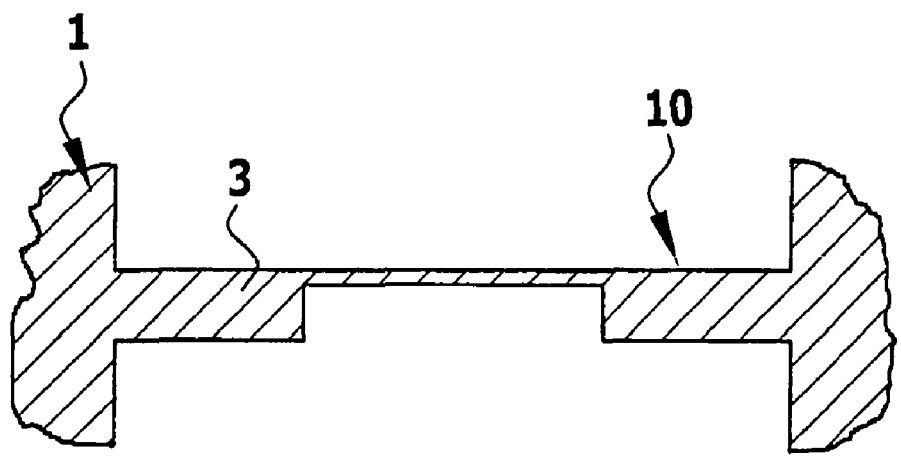
FIG. 33*b* is a view similar to FIG. 33*a* after an etching process.
Figure 34A:
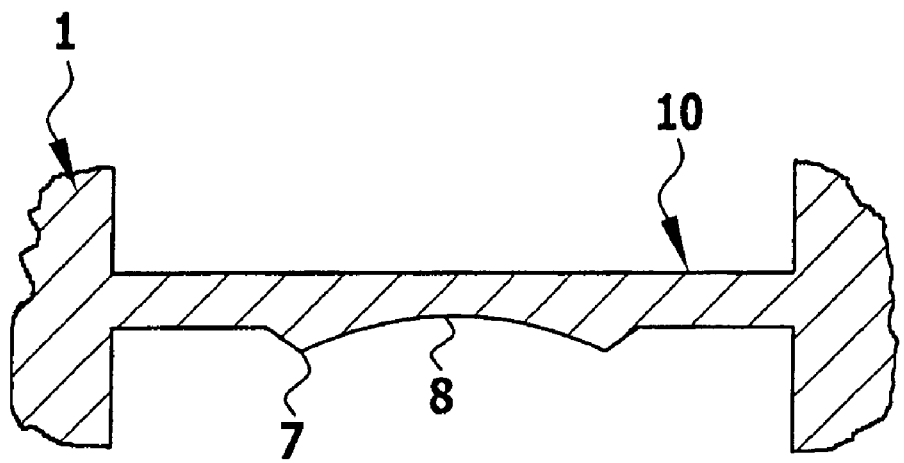
FIG. 34*a* is a view similar to FIG. 33*a* in the case of another cross-sectional form of the predetermined wall region.
Figure 34B:
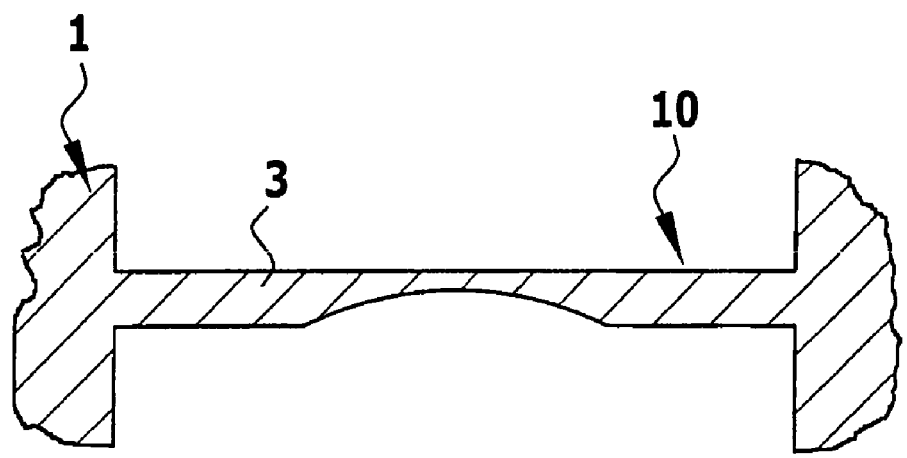
FIG. 34*b* is a view similar to FIG. 34*a* after the etching process.

FIGS. 33*a* and 34*a* show possible geometries of the predetermined wall regions 10, which are produced by a machining process, e.g. by milling or hollowing out. In this case, the remaining thickness of the material in the predetermined wall regions 10 is configured differently. In the exemplary embodiment of FIG. 33a, for example, a stepped depression 9 is arranged in the central wall region, in the exemplary embodiment of FIG. 34a a trough-like depression 9 with raised edges 7 is arranged. Thus, a membrane 3 with a thickness that is smaller in the central region than in the edge region is obtained after the etching process. If one works from a geometry according to FIG. 33a, then after the etching process a cross-section is obtained such as that shown in FIG. 33b, i.e. a cross-section with a stepped depression in the central region, if one works from a geometry such as that shown in FIG. 34a, a membrane with a cross-sectional face in keeping with FIG. 34b is obtained, i.e. with a central trough that merges without any step into the membrane surface.

The interior 2 or at least a part thereof is filled with a transfer medium, e.g. a gas or a liquid. By means of this transfer medium pressure fluctuations of the surrounding area that lead to a deformation of the membrane 3 are transferred to the interior 2 and there, inter alia, also to a microchip 4 arranged in the interior 2 (FIG. 5 and FIG. 5a).

Figure 5:
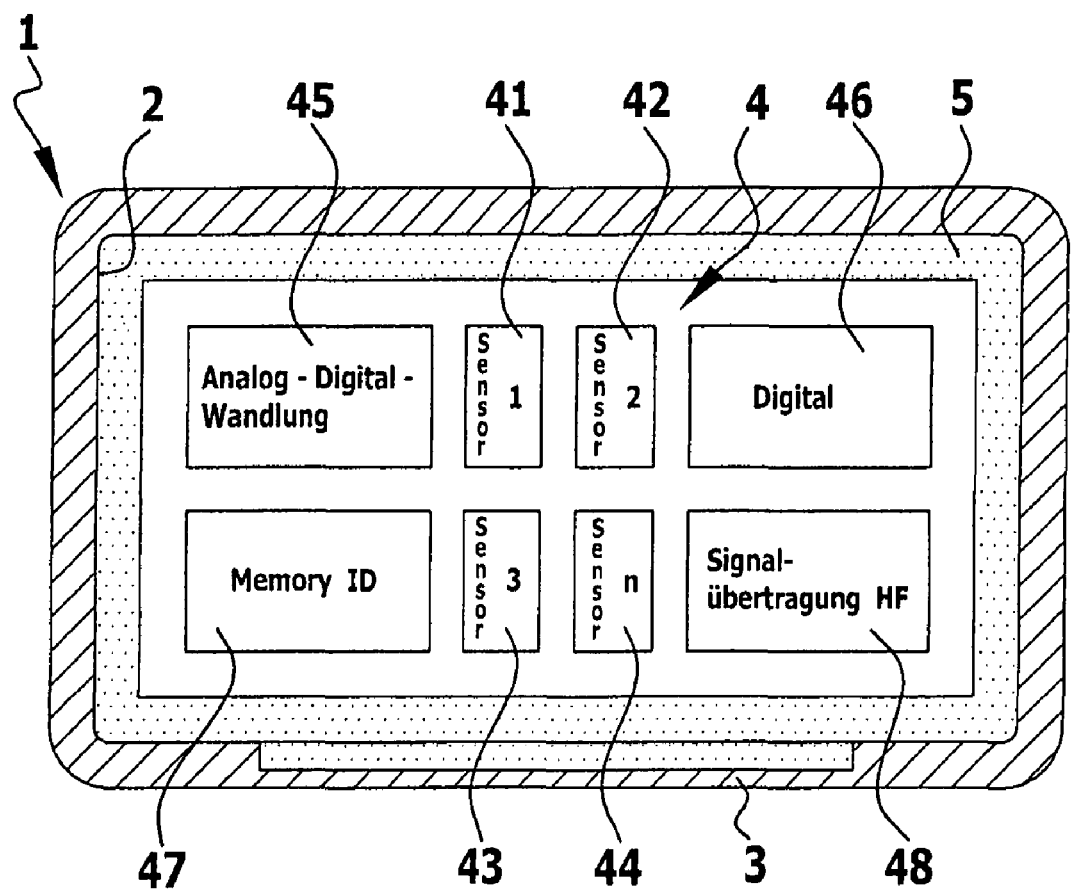
FIG. 5 is a schematic view of a rigid housing closed with a membrane with a microchip arranged therein with different function regions.
Figure 5A:
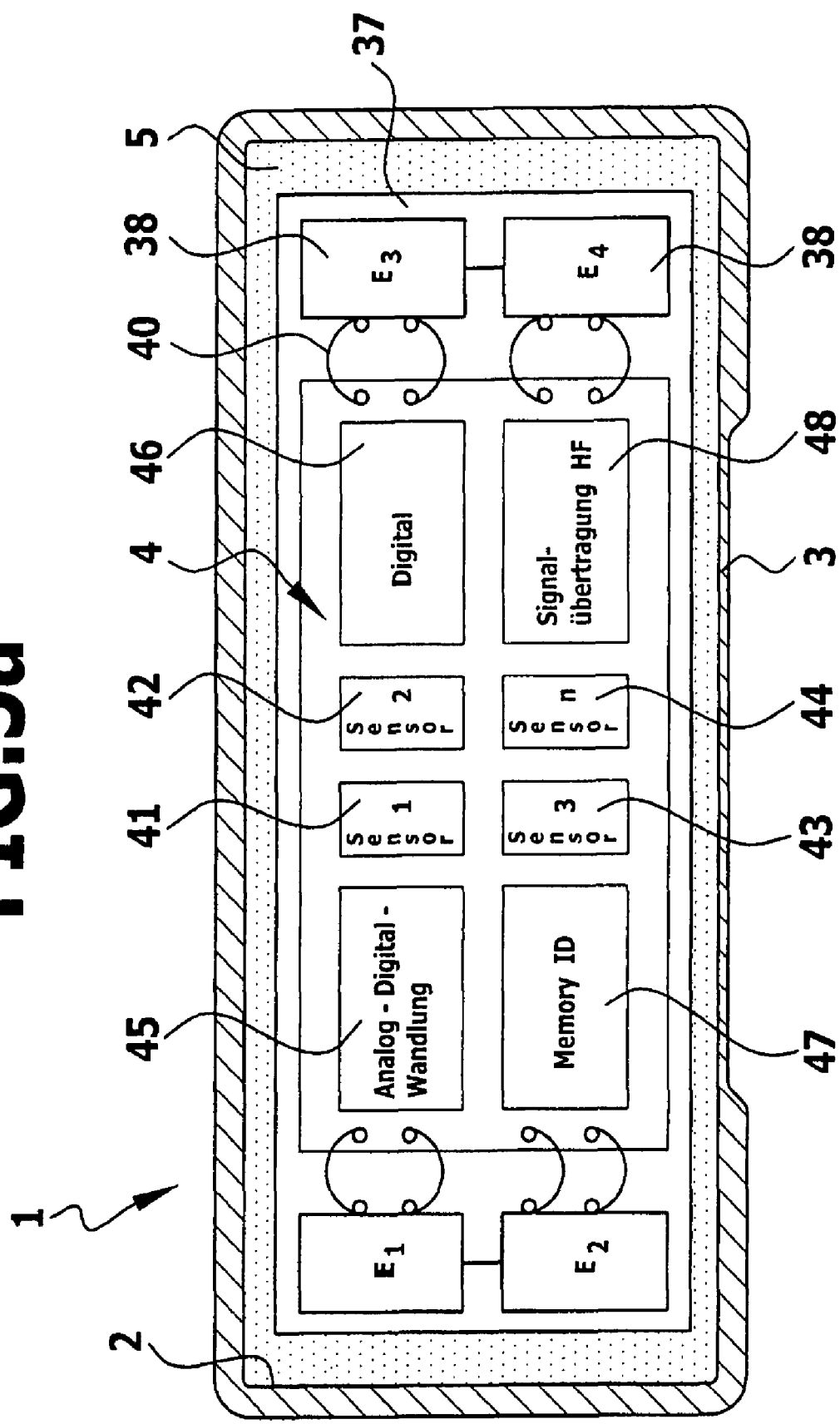
FIG. 5a is a view similar to FIG. 5 with a support receiving the microchip and additional electronic components.

The transfer medium 5 can preferably also be a vulcanised or polymerised plastic material, e.g. a cross-linked silicone, into which the microchip 4 is sealed and which completely fills the entire cavity between the microchip 4 and the inside wall of the housing 1, as is shown schematically in FIG. 5.

Figure 4:
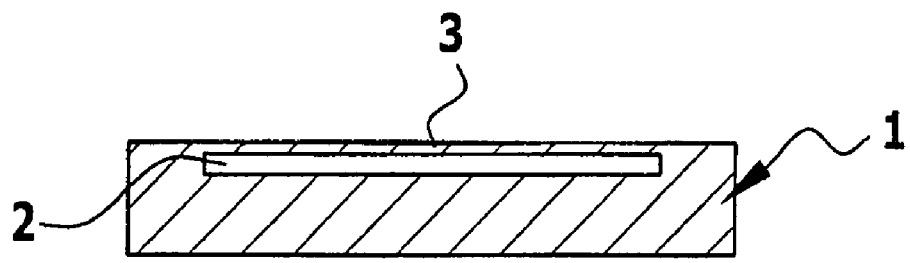
FIG. 4 is a view similar to FIG. 1 with a very small-volume interior surrounded by the housing.

In particular when a gas is used as transfer medium, it is favourable if the interior 2 is configured with a very small volume, as is shown in FIG. 4.

In principle, different measurement sites are established for the measurement of intracranial pressure. In most cases intraventricular measurement is recommended, corresponding exemplary embodiments are also conceivable for parenchymal, epidural or subdural measurement.

For intraventricular pressure measurement it is specifically recommended to use a titanium tube with an outside diameter of about 3 mm, which corresponds to the dimensions of a typical ventricle catheter normally used in hydrocephalus therapy. The housing is closed at the ends by a hemisphere. A window, which is closed again with an extremely thin metal foil, is formed in the cylindrical housing wall to be as close as possible to this semicircular tip (preferably about 1 to 3 mm away). The wall of the metal tube, which is made from a biocompatible material, has a thickness about 10-times that of the foil covering the window, but can also be configured to be even thicker. The thickness of the foil preferably amounts to 0.01 mm, the wall thickness of the tube 17 to 0.1 mm. The foil 21 is curved in keeping with the shape of the tube or clamped flat over the opening and welded to the tube, for example, by a laser welder to be gastight.

Figure 6:
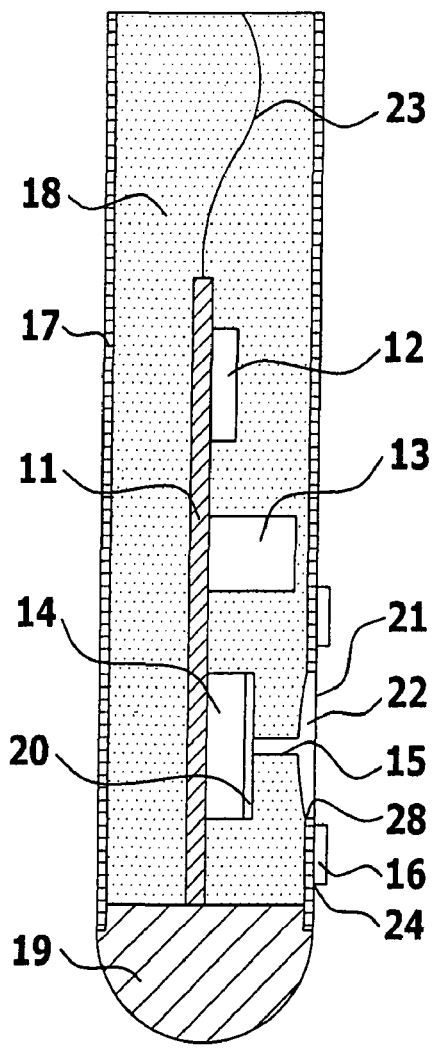
FIG. 6 is a schematic view in longitudinal section of a tubular housing with a membrane and a microchip arranged in the housing.
Figure 8:
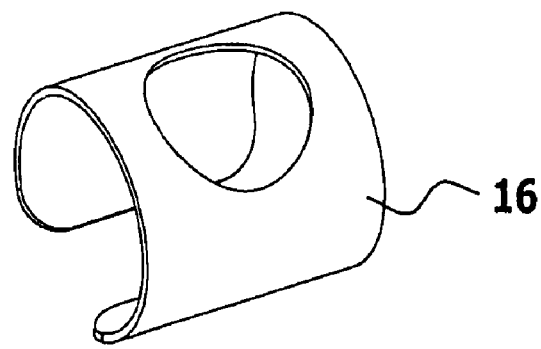
FIG. 8 shows a sleeve-like frame for sliding onto the tubular housing of FIG. 6.

The welding can preferably be performed with the aid of a clamping sleeve 16. FIG. 8 shows the structure of such a clamping sleeve. FIG. 6 shows the structure of a pressure sensor with clamping sleeve 16, microchip 4, electronics 12, 13 and air chambers 15, 20, 22. The clamping sleeve 16 has an inside diameter corresponding to the outside diameter of the tube 17 (thus of the housing). The thin foil 21 can be placed over the window in the tube 17 and secured by means of the clamping sleeve 16. The clamping sleeve 16 has an identical window to that of the tube 17. The clamping sleeve 16 is placed over the window so that the two windows lie precisely one over the other, wherein the window of the tube 17 is covered by the titanium foil. By welding the clamping sleeve 16 to the tube 17 along the outer edge 24, a gastight welding of the foil 21, tube 17 and clamping sleeve 16 is achieved. The quality assurance is achieved by means of a helium leak indicator.

The tube 17 is closed at the end with a cap 19 and welded. The electronic components are positioned on a support 11, and the transmission of the measurement signal is assured by a cable connection 23 to a coil 29.

Figure 10:
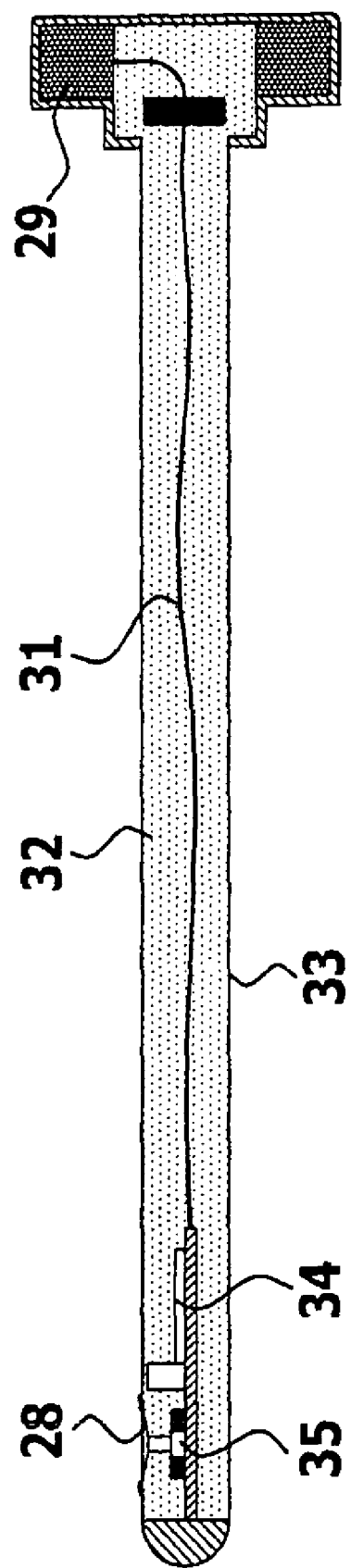
FIG. 10 is a schematic view in longitudinal section of the tube-shaped housing of FIG. 6 with transmission coil disposed therein.

FIG. 10 shows an overview of the implantable device. The externally prevailing pressure is transferred to the inside chamber 35 by way of the window 28 closed by the foil 21 and is measured by means of the electronic unit 34. A cable 31 passes the signal to the coil 29. A suitable shape of the housing 33 allows the housing 33 to be located in a drill hole in the cranium with a precise fit. The housing 33 is filled with a filler (preferably plastic, ceramic or metal) 32 as far as possible so that the space of the inside chamber 35 filled with gas is minimally small, so as to assure the most sensitive possible pressure transfer through the window 28.

Figure 7:
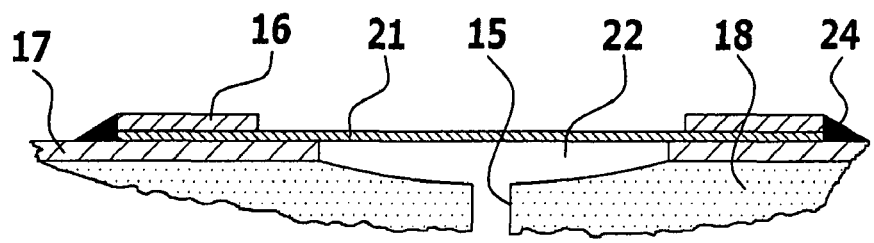
FIG. 7 is an enlarged detail view of the housing of FIG. 6 in the region of the membrane.

FIG. 7 shows an exemplary structure of a pressure window. The membrane or foil 21 is sealed to be gastight by means of the weld of the outer edge 24 with the clamping sleeve 16 and the tube 17. An air chamber 22, which is designed to be minimally small and which is connected to a chamber 20 (FIG. 6) by means of a duct-like air chamber 15, is located under the foil 21. The filler material 18 assures a minimally small air volume in the chambers 20, 22 and the air chamber 15.

Figure 9:
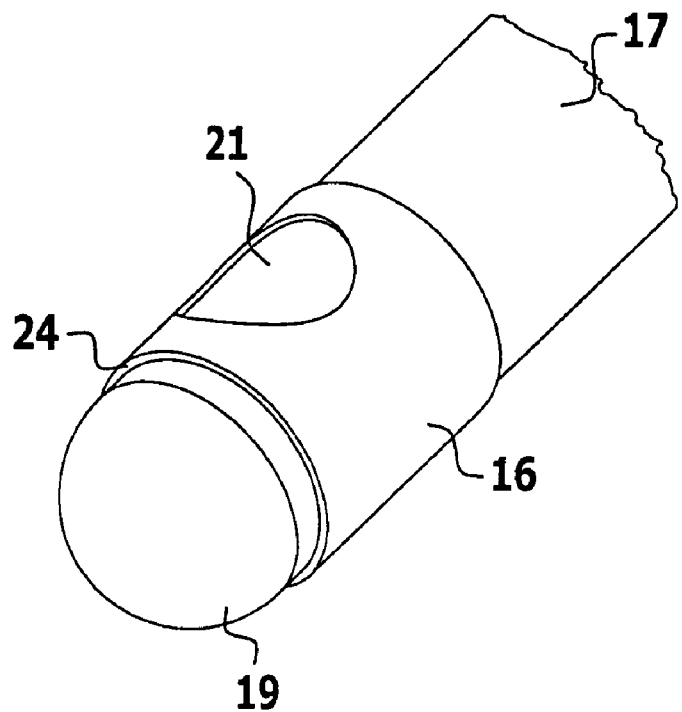
FIG. 9 is a perspective view of the lower end of the housing of FIG. 6 with sleeve-like frame slid thereon.

FIG. 9 shows a top view of the ventricle sensor with the cap 19, the welded outer edge 24, the clamping sleeve 16, the window with the thin foil 21 as well as the tube 17. FIG. 8 shows an exemplary embodiment for a clamping sleeve 16.

As shown in FIG. 5, the microchip can be an integrated chip, which has multiple function regions. One function region can be a pressure-sensitive sensor 41, for example, next to this other sensors 42, 43, 44 are indicated, e.g. one of these sensors can be a temperature sensor.

In addition, the microchip has an analog-to-digital converter 45, in which the analog electrical signals generated by the sensors are converted into digital signals.

In the shown exemplary embodiment, a digital sequential control means 46 is additionally provided as well as an identification panel 47, in which an unalterable, readable identification of the microchip 4 can be stored, by means of which the microchip 4 and thus the entire implantable device can be identified.

Finally, signal transmission elements 48 can be integrated into the microchip 4.

In the exemplary embodiment of FIG. 5a, a support 37 is additionally represented in the housing 1 in the form of a bend-resistant thin plate, on which the microchip 4 is attached, e.g. adhered. In addition to the microchip 4 the support 37 carries further electronic components 38, e.g. diodes or capacitors for power limiting, wherein these are passive electronic components in particular. Moreover, strip conductors 39 and band-type contacts 40 are arranged on the support 37 that connect the microchip 4 and the components 38 and also connect the components 38 to one another.

In all the embodiments it is possible to either arrange only one microchip in the housing 1, as is evident from the representation of FIG. 5, or a support 37, on which besides the microchip 4 further components 38 such as strip conductors 39 and contacts 40 are arranged.

In all the exemplary embodiments illustrated below this support can be additionally added to the microchip, but this is only shown in the drawings in the exemplary embodiment of FIG. 5a.

The microchip 4 can be arranged in the tube 17 in the same way as has been explained on the basis of FIG. 6.

However, it can also be provided that the housing 1 is so small in configuration that it is just large enough to receive the microchip 4, as is shown schematically in the example of FIG. 5. In this case, the microchip 4 fills almost the entire interior of the housing 1, the remaining interior space being filled with the transfer medium 5, in particular with a cross-linked silicone or a highly viscous oil. The sensors 41 to 44 and in particular the pressure-sensitive sensor 41 are located approximately in the centre of the housing 1, as is also shown in FIG. 5. The housing 1 can be cylindrical with an outside diameter in the order of between 2 and 5 millimeters, in particular about 3 millimeters, and a length of between 15 and 25 millimeters, in particular about 20 millimeters. Therefore, this is a very small structural unit, which can be placed in a simple manner at the desired position in the brain.

Figure 18:
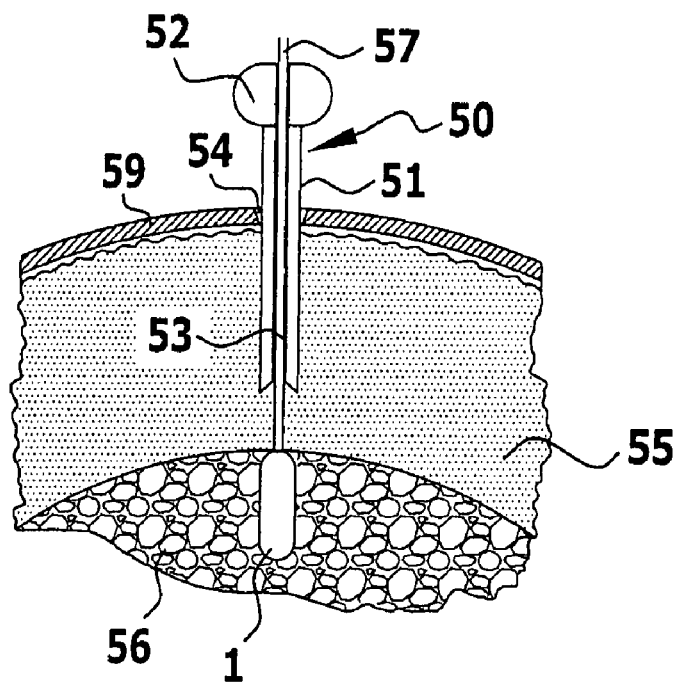
FIG. 18 is a representation similar to FIG. 16 after placement of the rigid housing in the brain and during withdrawal of the manipulation tool.
Figure 19:
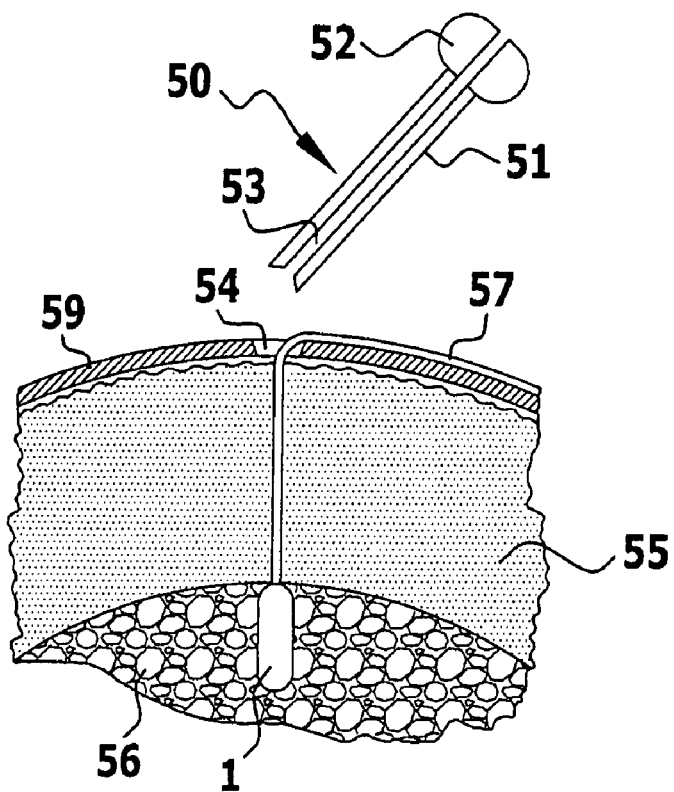
FIG. 19 is a view similar to FIG. 16 with the rigid housing in place and after the manipulation tool has been withdrawn.

This placement can be achieved by means of a manipulation instrument 50, as is shown schematically in FIGS. 16 to 19. This is a tube 51 with a handle 52, the outside wall of which has a through longitudinal slot 53. The housing 1 is inserted into the tube 51 at the front end of the manipulation instrument 50 and is held there, e.g. by clamping. The manipulation instrument 50 with the housing 1 held therein is placed through a drill hole 54 in the top of the cranium 55 at the desired location of the brain 56 (FIG. 17), and the manipulation instrument 50 is then pulled back out of the drill hole 54, wherein the housing 1 remains in the brain 56 (FIG. 18). In this case, the longitudinal slot 53 serves to insert a connection cable 57 arranged on the housing 1 into the tube 51 and pull this out again after placement of the housing 1, so that the manipulation instrument 50 can be completely separated from the housing 1 after it has been located (FIG. 19).

Figure 11:
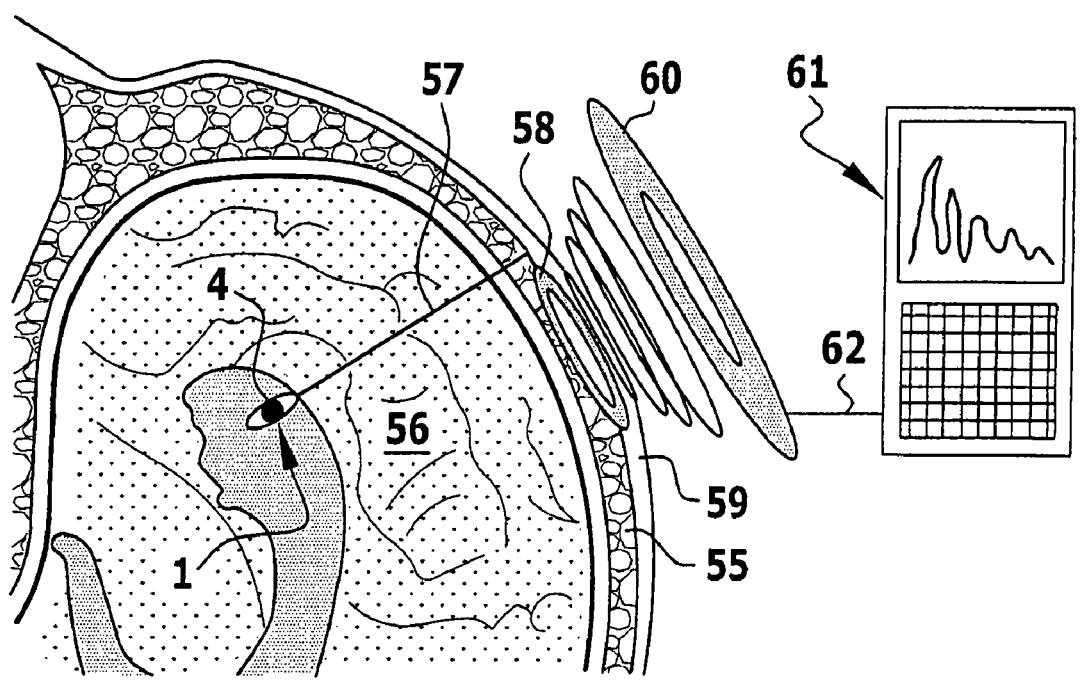
FIG. 11 is a schematic representation of a rigid housing placed inside the brain with the microchip arranged therein and a transmission coil arranged on the cranial bone.
Figure 12:
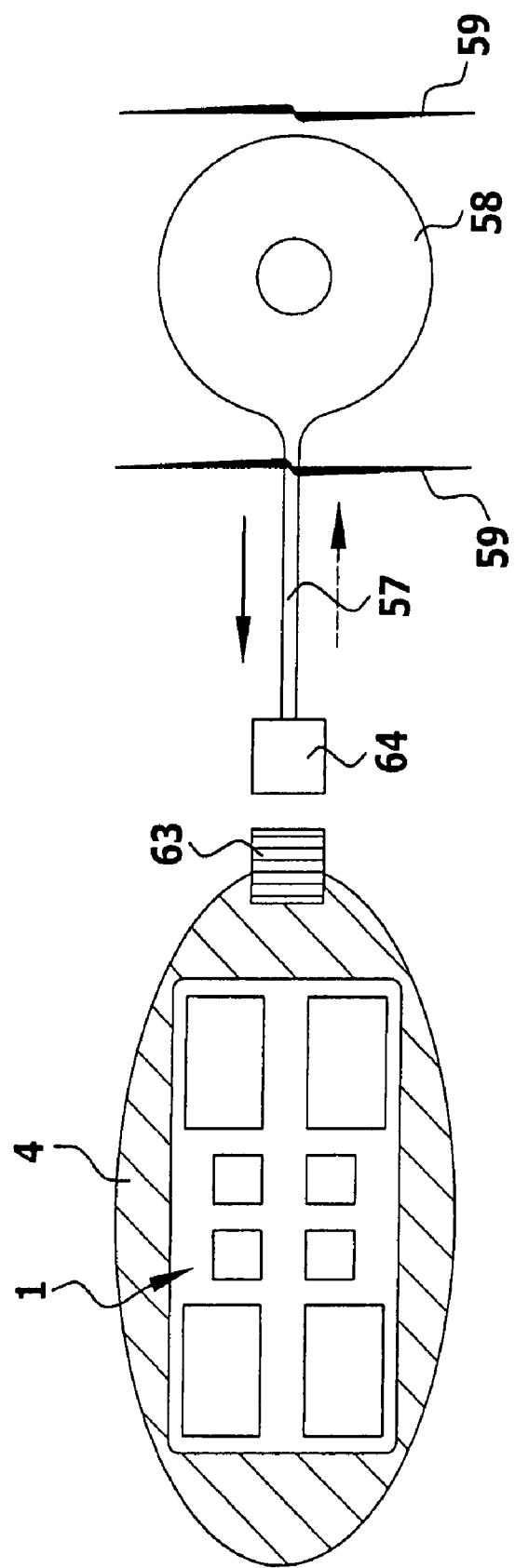
FIG. 12 is a schematic detail view of the implantable device of FIG. 11.

FIG. 11 shows the housing 1 placed in the brain 56 in this manner and a connection cable 57, which leads from the housing 1 onto the outside of the top of the cranium 55 and is connected to a coil 58, which is laid externally on the top of the cranium 55, i.e. between the top of the cranium 55 and the scalp 59, or in an alternative embodiment externally on the scalp 59. FIG. 12 shows both alternatives by showing the scalp 59 twice, namely once on one side and once on the other side of the coil 58.

This coil 58 can be coupled inductively to a transmission coil 60, which is brought externally onto the scalp 59, so that an electrical connection can be created by means of the two coils 58 and 60 to an evaluation unit 61, which is connected to the transmission coil 60 by means of a line 62.

The coil 29 in the exemplary embodiment of FIGS. 6 to 10 is connected to an evaluation unit in a similar manner.

However, this connection can also be replaced by an electrical connection, with which the connection cable 57 coming from the housing 1 is not connected to a coil 58, but directly to an evaluation unit outside the body, e.g. one carried on the body. In this case, the connection cable 57 passes through the scalp.

In the exemplary embodiment of FIGS. 6 to 10, the coil 29 is embedded into the housing 33, so that an electrically conductive connection between the microchip 4 and the coil 29 can be made inside the housing.

The situation is different in the configurations of FIG. 5 or 5a, in which only the microchip 4 or the support 37 with the microchip 4 are arranged in the housing 1, a connection cable 57 that must be guided out of the housing 1 is necessary here. This bushing is configured so that the interior of the housing 1 is hermetically sealed in this exit region. This can be achieved, for example, by means of a support made of ceramic or plastic, which is inserted into the housing wall and is sealed relative to this and into which electrical contacts are embedded. An adhesive or gold solder can be used for sealing.

The connection cable 57 can be permanently connected to the contacts of the hermetic duct, e.g. by soldering, welding, contact adhesion, crimping or other connection techniques known per se.

In another configuration a releasable connection can also be provided between the hermetic duct and the connection cable, e.g. by using a plug connection. Such a plug contact 63, which passes tightly through the wall of the housing 1 and to which the connection cable 57 can be attached by means of an appropriate counterpart 64, is schematically shown on the housing 1 in the exemplary embodiment of FIG. 12.

Figure 13:
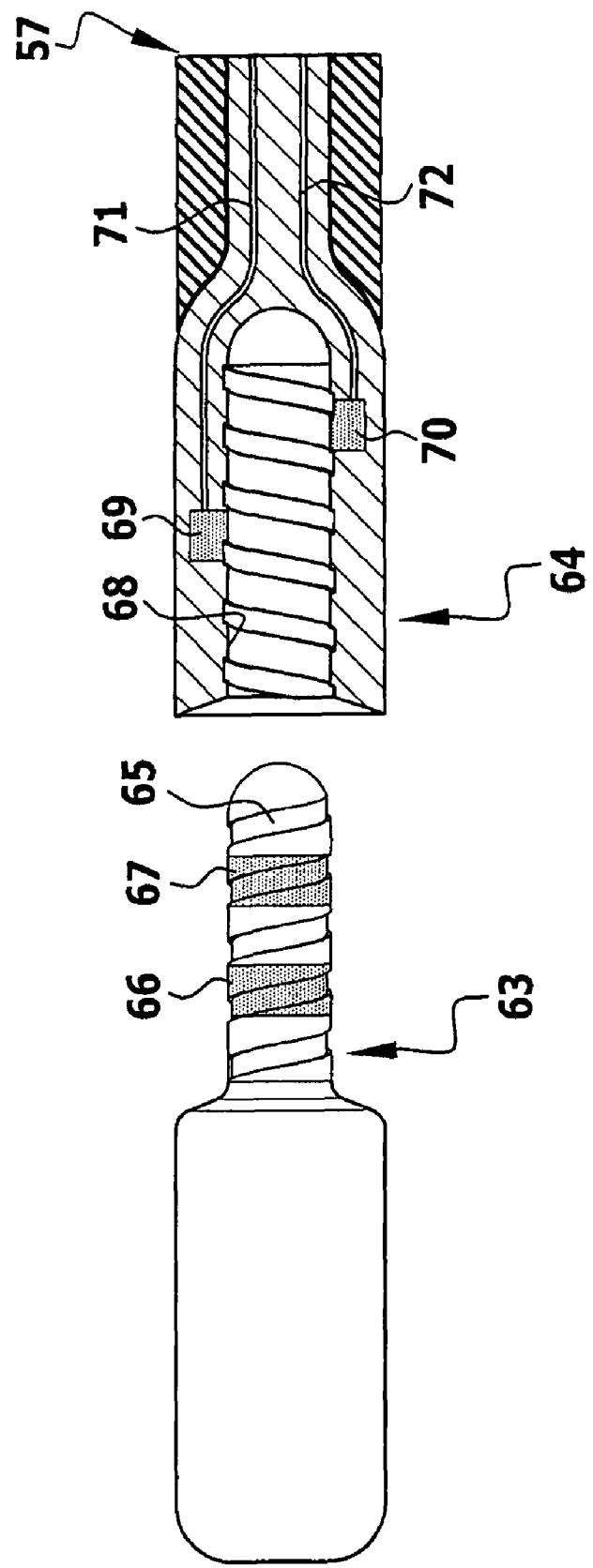
FIG. 13 is a schematic view of a connection means of a power and signal line between the rigid housing and the transmission coil in the implantable device of FIG. 11.

An exemplary embodiment of such a plug contact 63 and a corresponding counterpart 64 is shown in FIG. 13.

The plug contact 63 arranged on the housing 1 has an externally threaded stem 65, which bears two contact regions 66, 67 electrically insulated from one another, which connect to the microchip 4 via separate lines.

The counterpart 64 has an internally threaded stem 68, so that the counterpart can be screwed onto the externally threaded stem 65. When these are fully tightened, two contact regions 69 and 70 come into electrically conductive abutment against the contact regions 66 or 67, so that an electrical connection is created in these contact regions. The contact regions 69 and 70 of the counterpart 64 are connected to conductors 71, 72 of the connection cable 57.

After tightening, the counterpart 64 completely closes off the externally threaded stem 65 and seals this relative to the surrounding area. This results not only in a hermetically tight bushing through the wall of the housing, but also a hermetically tight connection of the plug contact 63 with the counterpart 64.

This connection can naturally also be configured as a simple plug connection, therefore the term plug contact is used. However, the described screw connection is advantageous, because any unintentional release of the connection is prevented as a result.

Figure 14:
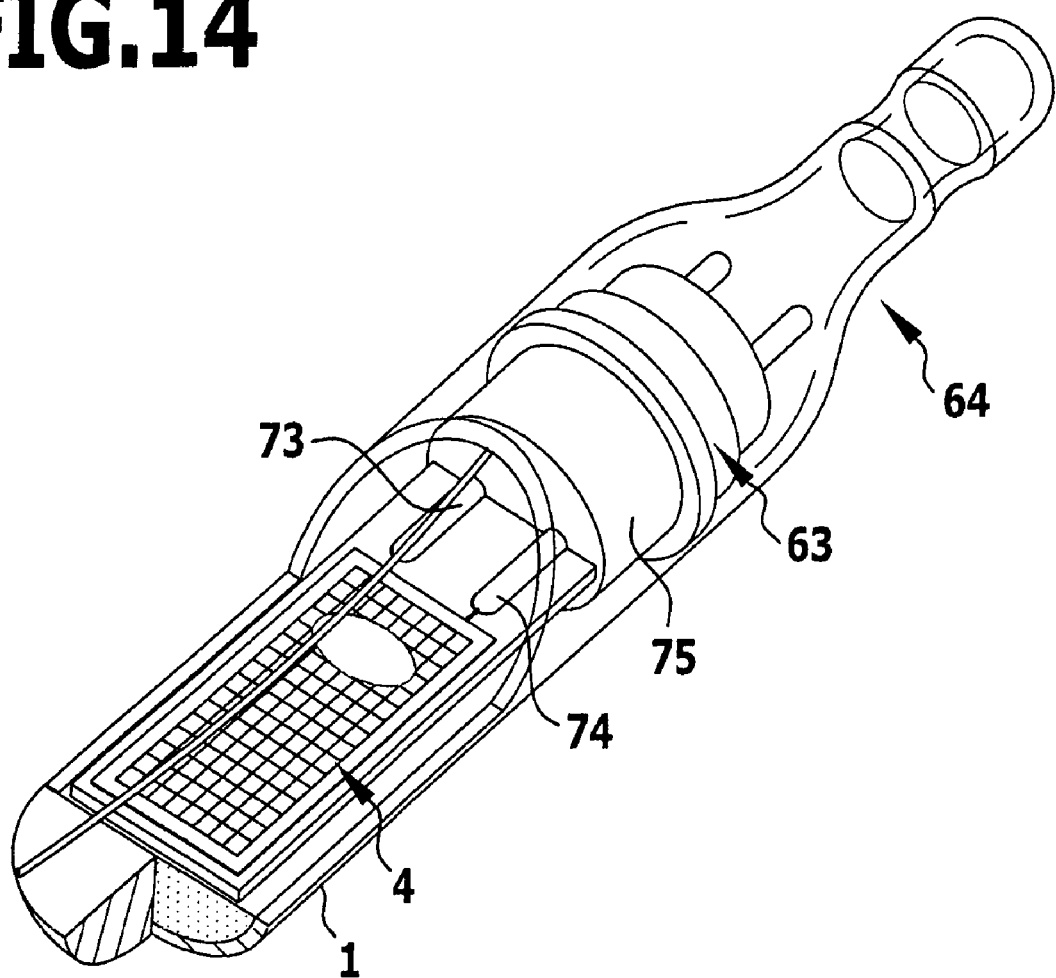
FIG. 14 is a perspective view in partial section of a preferred exemplary embodiment of a rigid housing with the microchip received therein.

FIG. 14 shows an exemplary embodiment of such a housing 1, which receives in its interior the microchip 4 that connects directly with contact pins 74, 75. These pass tightly through a support 75, which is inserted tightly into the wall of the housing 1 and on which a counterpart 64 is attached. The contact pins 73, 74 can also be permanently connected directly to the connection line, e.g. by welding, soldering, contact adhesion, crimping or other techniques.

In its remaining interior the housing 1 is filled with a highly viscous oil or a cross-linked silicone and transmits movements of the membrane (not shown in FIG. 14) onto the sensors of the microchip 4 in the described way.

The entire arrangement shown in FIG. 14 has a diameter in the order of 3 millimeters and a length in the order of 20 millimeters, i.e. constitutes a very small structural unit.

Figure 15:
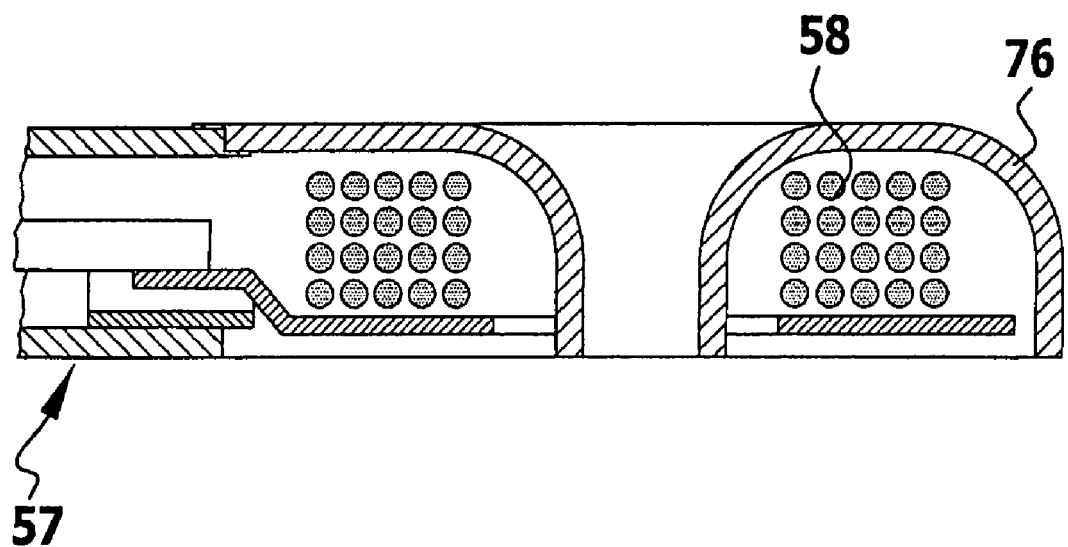
FIG. 15 is a sectional view through a transmission coil.
Figure 16:
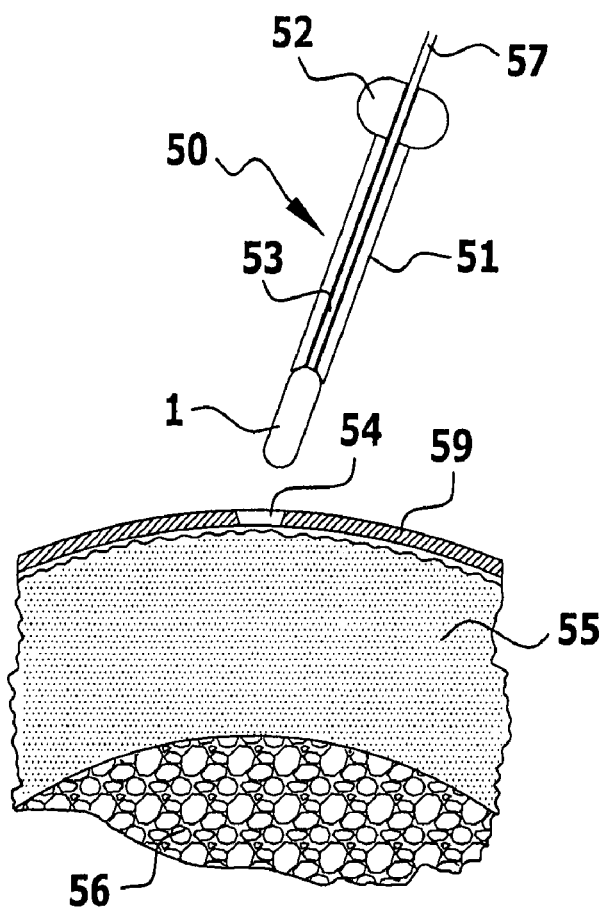
FIG. 16 shows a manipulation tool for implantation of the rigid housing into the brain before insertion of the rigid housing into the interior of the brain.
Figure 17:
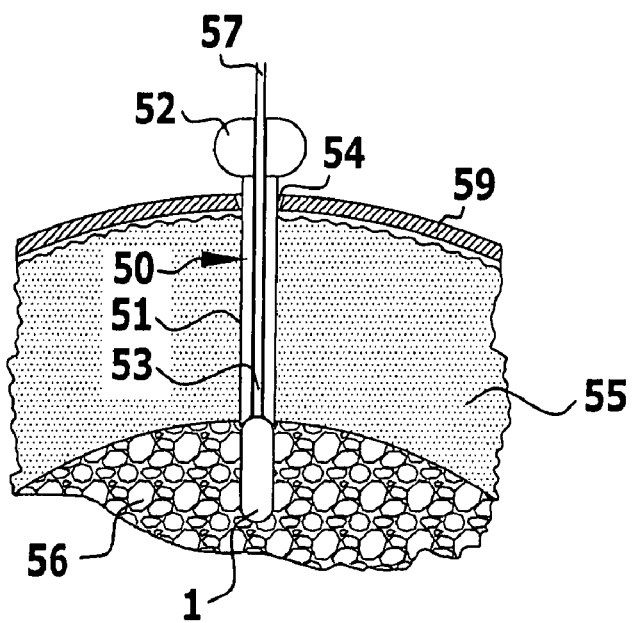
FIG. 17 is a representation similar to F*igure* 16 during advancing of the rigid housing into the brain.

If the connection cable 57 is connected to a coil 58 at its end remote from the housing 1, then this can be achieved in a manner clearly shown in the representation of FIG. 15. The coil is received in an annular housing 76 that is closed on all sides, the connection cable 57 feeds laterally into the housing 76 to form a seal and is connected to the coil 58 there. A very flat arrangement results, which can be placed in this form on the cranial bone, i.e. between the cranial bone and the scalp, as is clear from the representation of FIG. 11.

Power can be supplied to the microchip 4 from the outside via the coil 58 and the connection cable 57, so that the microchip does not require a power supply of its own. On the other hand, digital signals generated by the sensors of the microchip 4 can be transmitted via the connection line to the evaluation unit. The connection cable 57 thus constitutes a power and signal transmission line.

Figure 20:
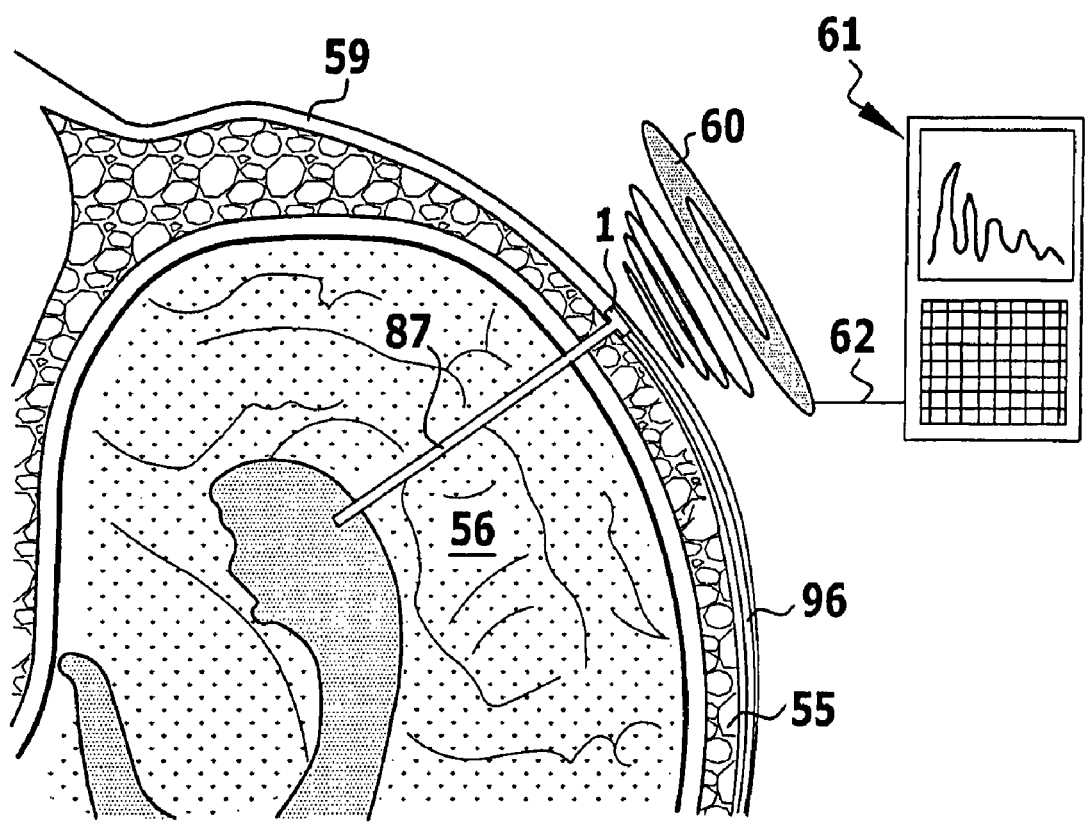
FIG. 20 is a view similar to FIG. 11 with a rigid housing arranged outside the cranial bone and a connection tube extending into the interior of the brain.
Figure 21:
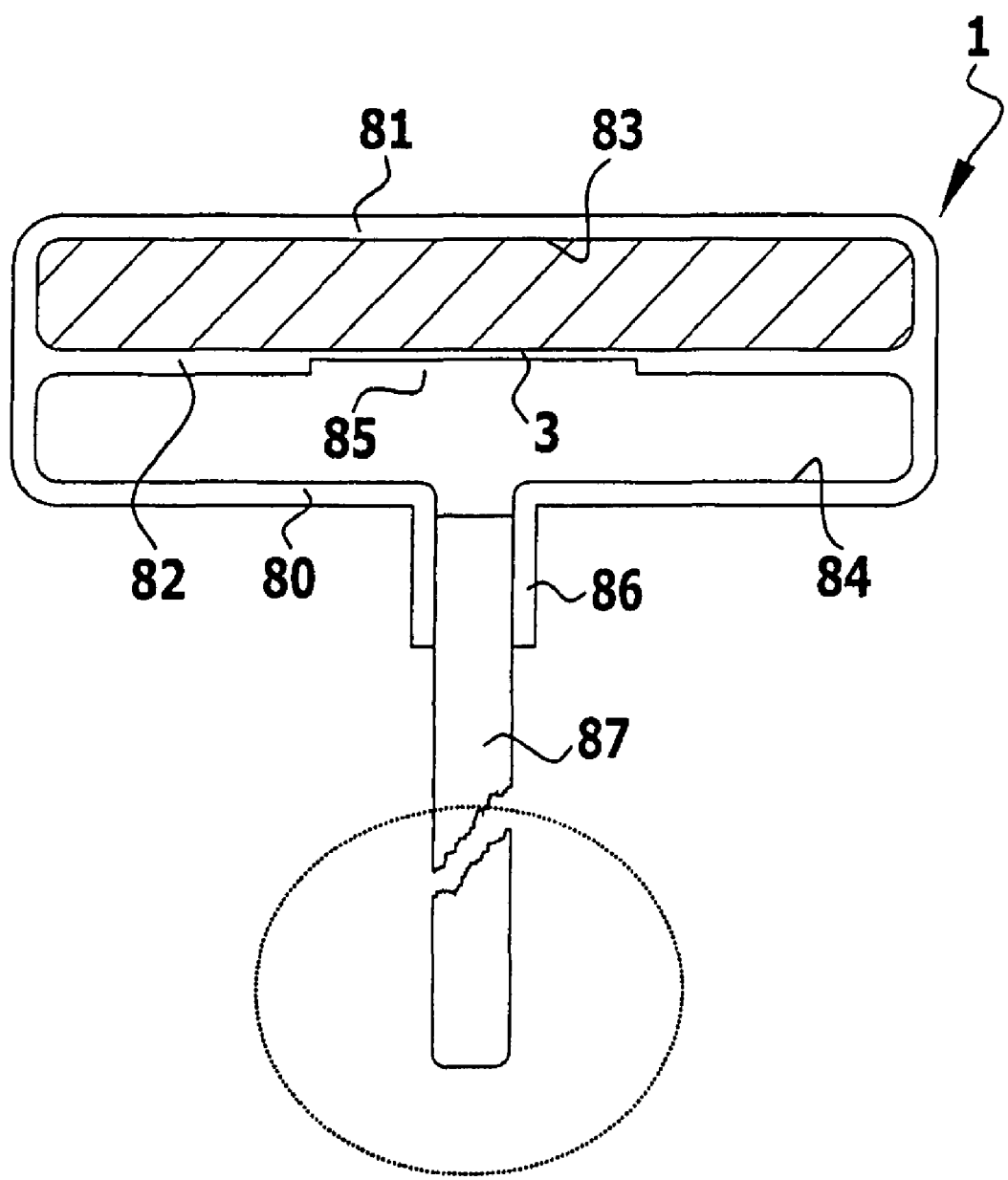
FIG. 21 is a schematic sectional view through a rigid housing with a measurement chamber and a fluid chamber.

A further preferred embodiment of an implantable device for intracranial pressure measurement is shown in FIG. 20 et seq. In this case, the housing 1 of this device is in the form of a shallow can with a plane floor surface 80 and an upper side 81 that is also plane in the exemplary embodiment shown. In this case, the housing is circular in cross-section with a diameter of between 1 cm and 3 cm, the height amounting to between about 2 mm and 5 mm. The housing 1 is divided into an upper measurement chamber 83 and a lower fluid chamber 84 by an intermediate wall 82 running parallel to the floor surface 80. The intermediate wall 82 is opened in the central region, and this connection region 85 between the measurement chamber 83 and the fluid chamber 84 is closed off by the membrane 3.

At the lower end of the fluid chamber 84 a pipe connection 86 exits in the centre of the housing 1 to project vertically downwards, and this is connected to an elongated tube 87 that forms a catheter.

A microchip 4 is arranged in the measurement chamber 83, as in the housings of the above-described embodiments, the measurement chamber 83 being filled with a transfer medium 5, preferably a cross-linked silicone. In this way, the pressure of a liquid in the fluid chamber 84 can be measured by means of the membrane 3 and a corresponding measurement signal can be generated.

The described device is placed on the head in such a manner that the tube 87 is advanced at its free end in the manner of a catheter to the location of the brain, at which the intracranial pressure is to be measured. The housing 1 lies on the outside of the top of the cranium 55 with its floor surface 80, the pipe connection 86 and the tube 87 then project through the drill hole 54 in the top of the cranium 55, as is shown schematically in FIG. 20. The housing 1 thus serves as a drill hole covering. The tube 87 is open at its end remote from the housing 1 and thus allows brain fluid to flow into the fluid chamber 84. When completely full, the pressure of the brain fluid at the location of entry is transferred via the membrane 3 to the microchip 4 in the measurement chamber 83.

Figure 29:
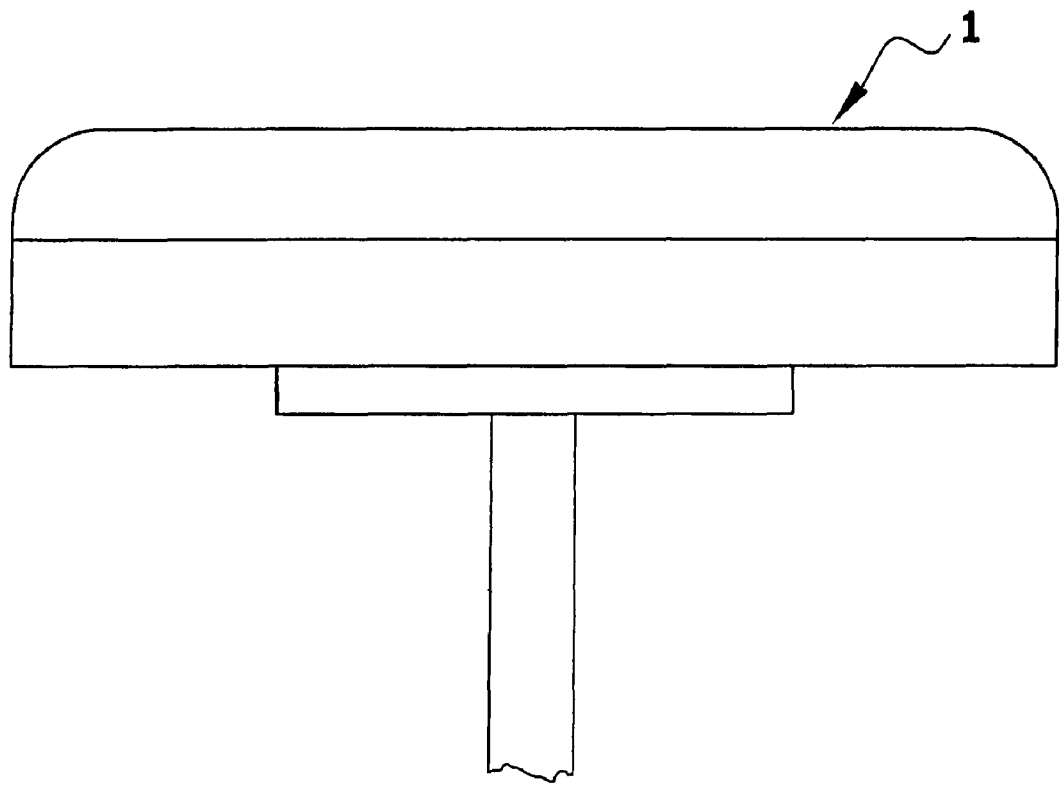
FIG. 29 is a schematic side view similar to FIG. 21 with a catheter-type extension closed off by the membrane.

However, as shown in FIG. 29, the tube 87 could also be closed and have an opening 90 closed by a membrane 89 at its closed end 88. In this embodiment, the fluid chamber 84 and the tube 87 are filled with a further transfer medium, e.g. a liquid, and the pressure of the surrounding brain fluid is transferred via the membrane 89 to the liquid filling in the fluid chamber and in the tube 87. In this way, the pressure is transferred by the transfer medium to the membrane 3 and thus to the microchip 4.

The digital signals generated by the microchip are transmitted to the transmission coil 60 either via a coil 91 arranged in the measurement chamber 83 or are passed electrically or inductively to the evaluation unit by means of a connection cable 57 directed out of the housing 1 to form a seal.

In the exemplary embodiments of FIGS. 22, 23, 25 and 26, the coil 91 surrounds the microchip concentrically inside the measurement chamber 83, so that a particularly favourable division of space results, which contributes to a small structural size of the housing 1.

Figure 30:
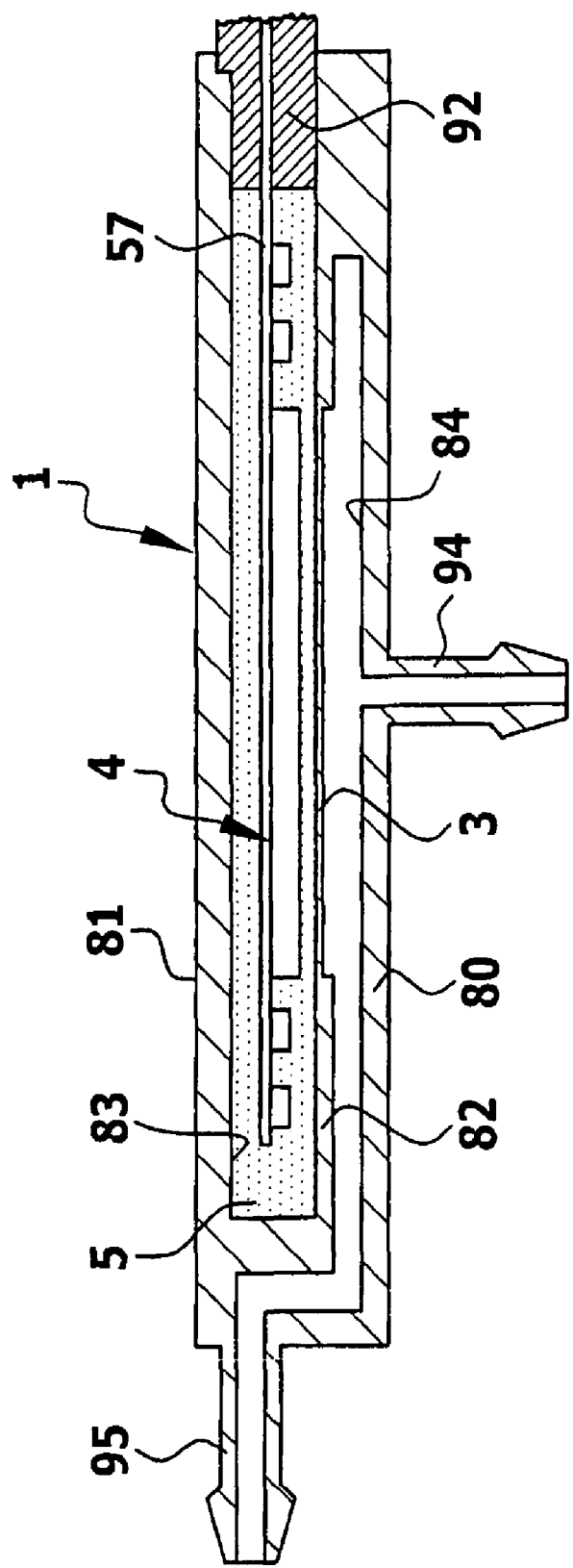
FIG. 30 is a schematic sectional view of a rigid housing similar to FIG. 23, but without a transmission coil in the interior of the rigid housing.
Figure 31:
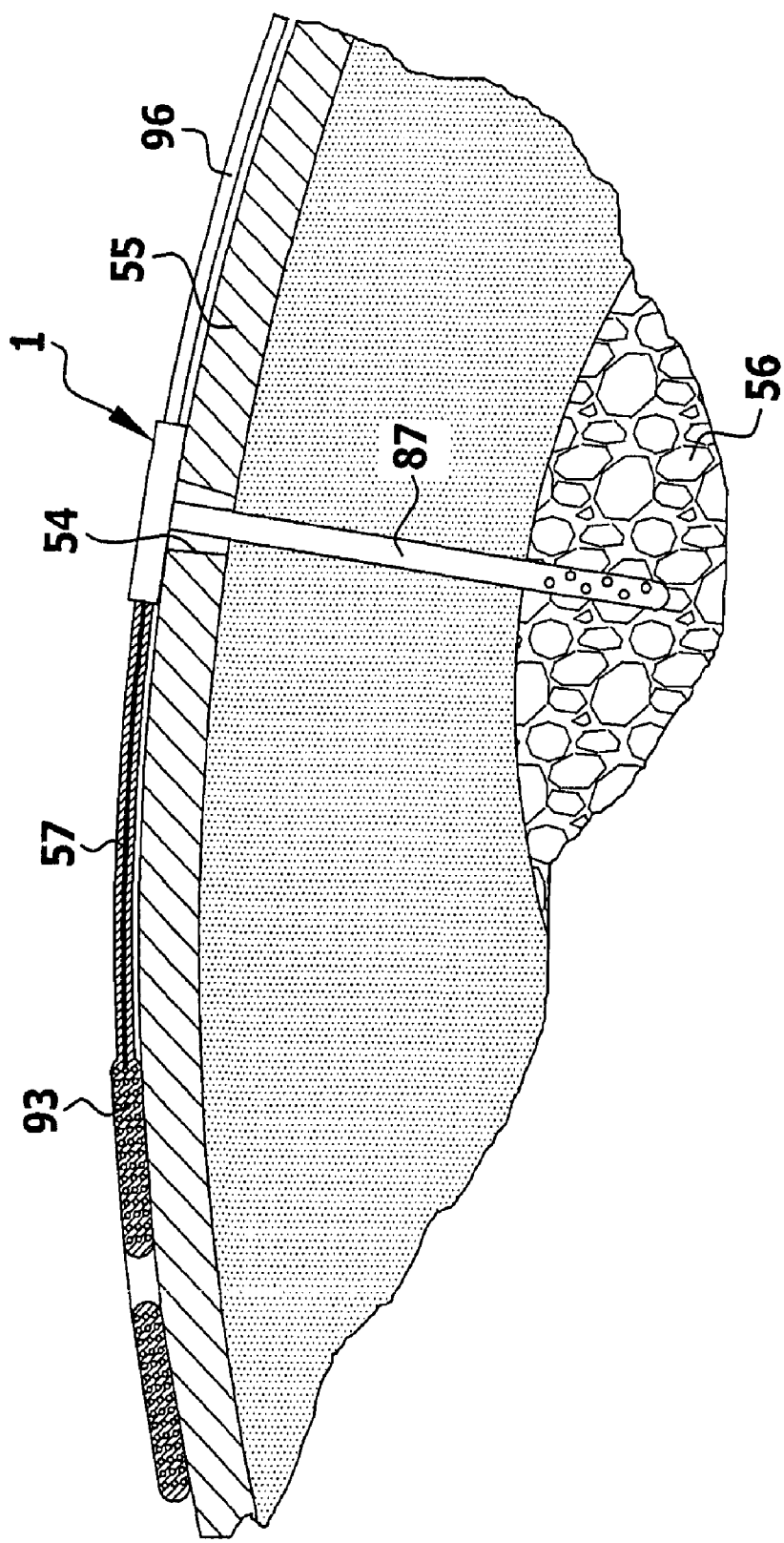
FIG. 31 is a schematic representation of a rigid housing covering a drill hole in the top of the cranium with a transmission coil laid on the top of the cranium next to the rigid housing.
Figure 32:
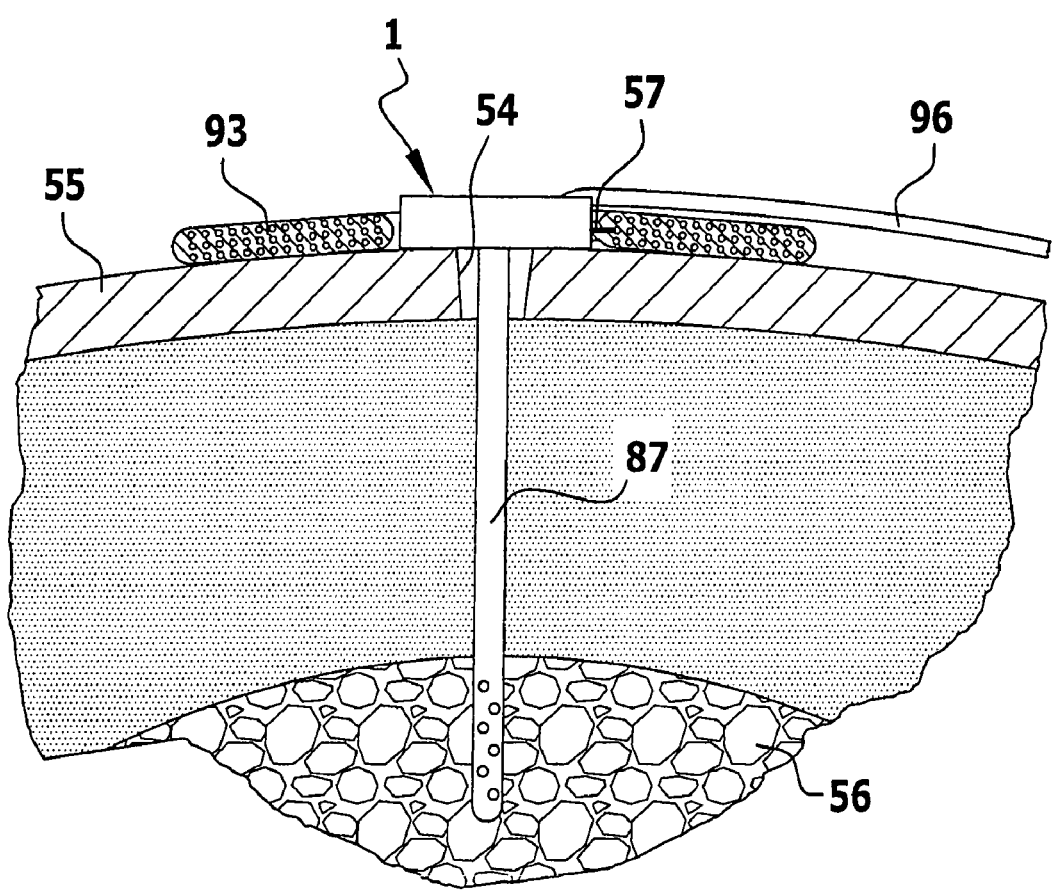
FIG. 32 is a view similar to FIG. 31 with a transmission coil surrounding the rigid housing.

In contrast, a connection cable 57 leading out of the housing 1 is provided in the exemplary embodiments of FIGS. 30, 31 and 32. In this case, the housing 1 is provided with a sealed cable duct 92 in the exit region that can also be configured in the manner explained on the basis of the other exemplary embodiments. The connection cable can lead directly to a coil 93, which is placed on the outside of the top of the cranium 5 outside the housing 1, i.e. either at a distance from the housing 1 next to this (FIG. 31) or to concentrically surround the housing 1 (FIG. 32).

Naturally, the connection cable 57 could also be directly electrically connected to the evaluation unit 61.

Figure 22:
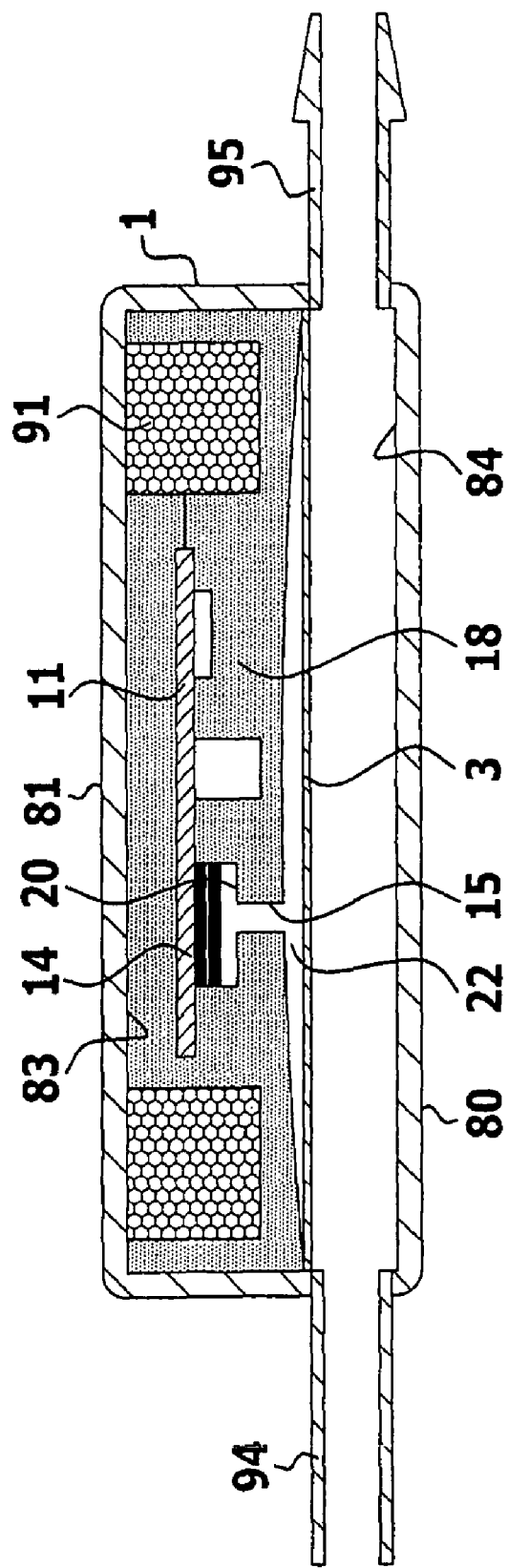
FIG. 22 is a sectional view of a preferred exemplary embodiment of a rigid housing with a measurement chamber receiving a microchip and a fluid conduit passing through the fluid chamber.

The described design is suitable in particular for determining the fluid pressure in a drainage system for the treatment of hydrocephalus. FIG. 22 shows an overview diagram of such a structure. With this device, the measurement chamber of which is of similar structure to that in the exemplary embodiment of FIG. 6, but additionally receives a coil 91, the intermediate wall 82 is replaced by the membrane 3, i.e. the membrane 3 extends over the entire cross-section of the housing 1 and divides the interior of the housing 1 into the measurement chamber 83 and the fluid chamber 84. Such a configuration can also be used in the other can-shaped housings 1, but a configuration with an intermediate wall 82 and a membrane 3 inserted into this can also be used in all such can-shaped housings.

Figure 27:
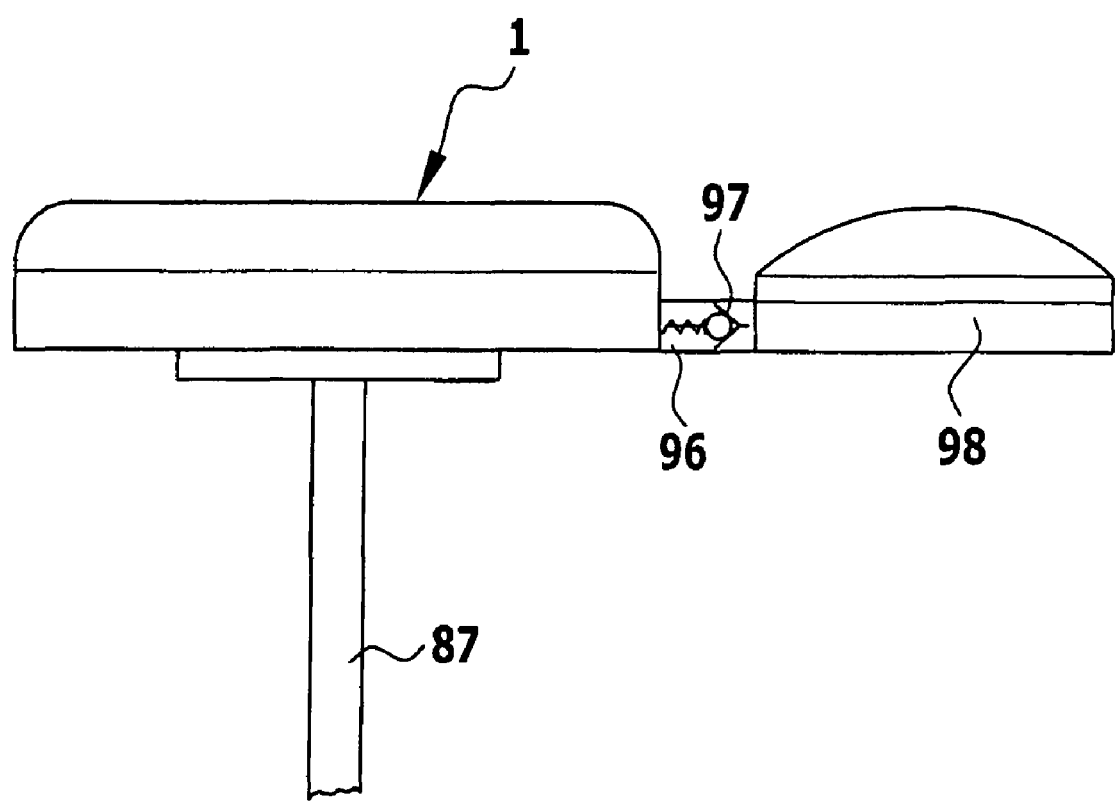
FIG. 27 is a schematic side view of the rigid housing of FIG. 23 with a non-return valve in the drainage pipe and a liquid reservoir connected to the drainage pipe.

In the exemplary embodiment of FIG. 22 two pipe connections 94, 95 running parallel to the floor surface 80 branch off from the fluid chamber 84 on opposite sides, one of which pipe connections is connected to a tube 87 and forms the liquid supply pipe, whereas the other can be connected to a liquid drainage pipe, which is only shown schematically in FIGS. 31 and 32. Thus, the brain pressure fluid can flow out of the interior of the cranium through the fluid chamber 84 and be removed from the interior of the cranium, as is usual in drainage systems for the treatment of hydrocephalus. As shown schematically in FIG. 27, a non-return valve 97 can be inserted into a drainage pipe 96, the drainage pipe can terminate in a reservoir 98, in which the drained liquid is collected. This reservoir can be used, for example, to backwash and clean the liquid pathways.

Figure 28:
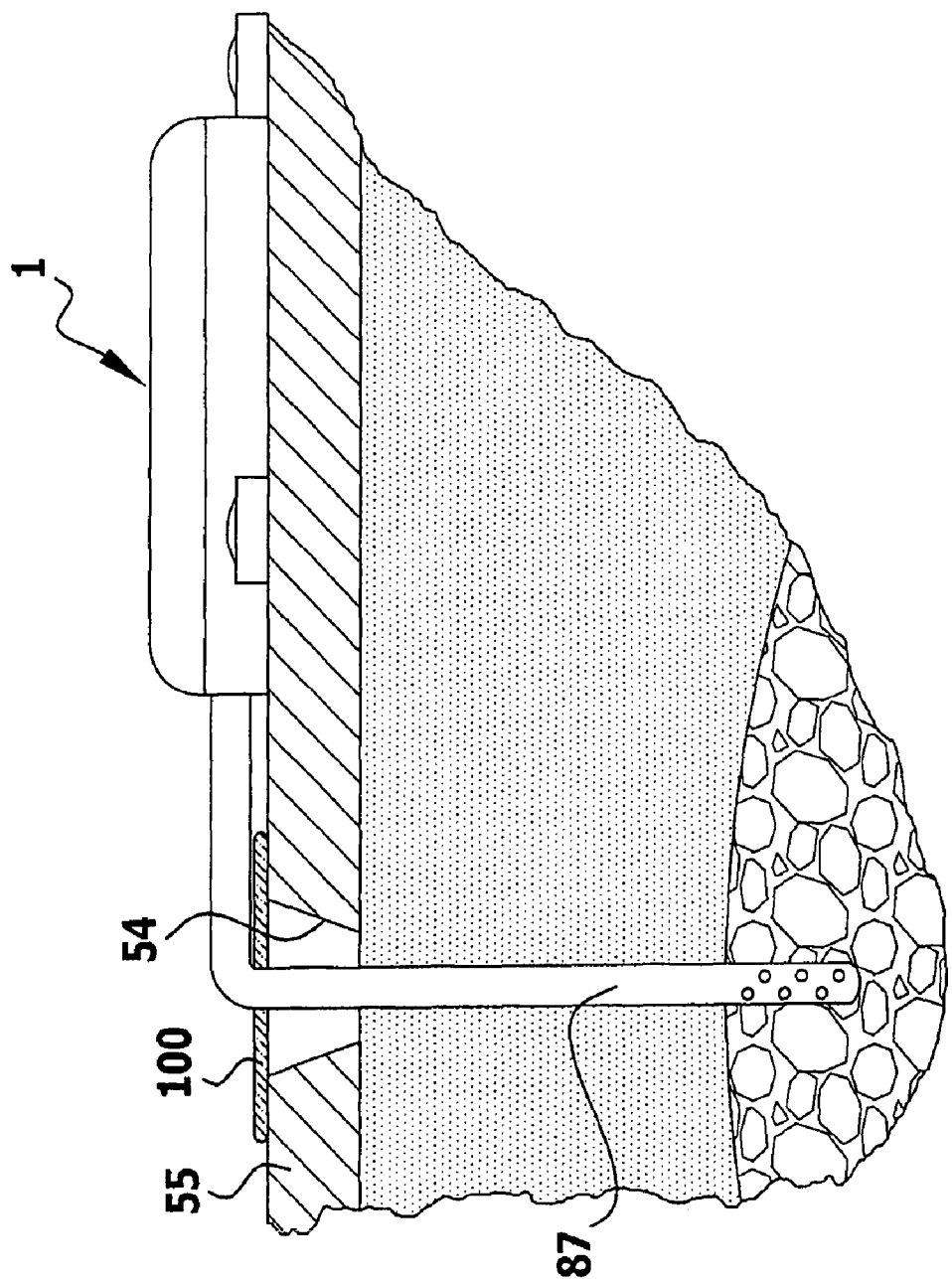
FIG. 28 is a schematic representation of a rigid housing arranged next to a drill hole in the top of the cranium and a supply conduit passing through the drill hole into the brain.

In the case of a housing 1 with a supply conduit entering the fluid chamber 84 parallel to the floor surface 80, it is favourable not to arrange the housing 1 directly above a drill hole 54, but laterally next to a drill hole, so that the drill hole remains free for the passage of the supply conduit, as is shown in FIG. 28. A separate drill hole covering 100 can then be provided in the region of the drill hole 54.

Figure 23:
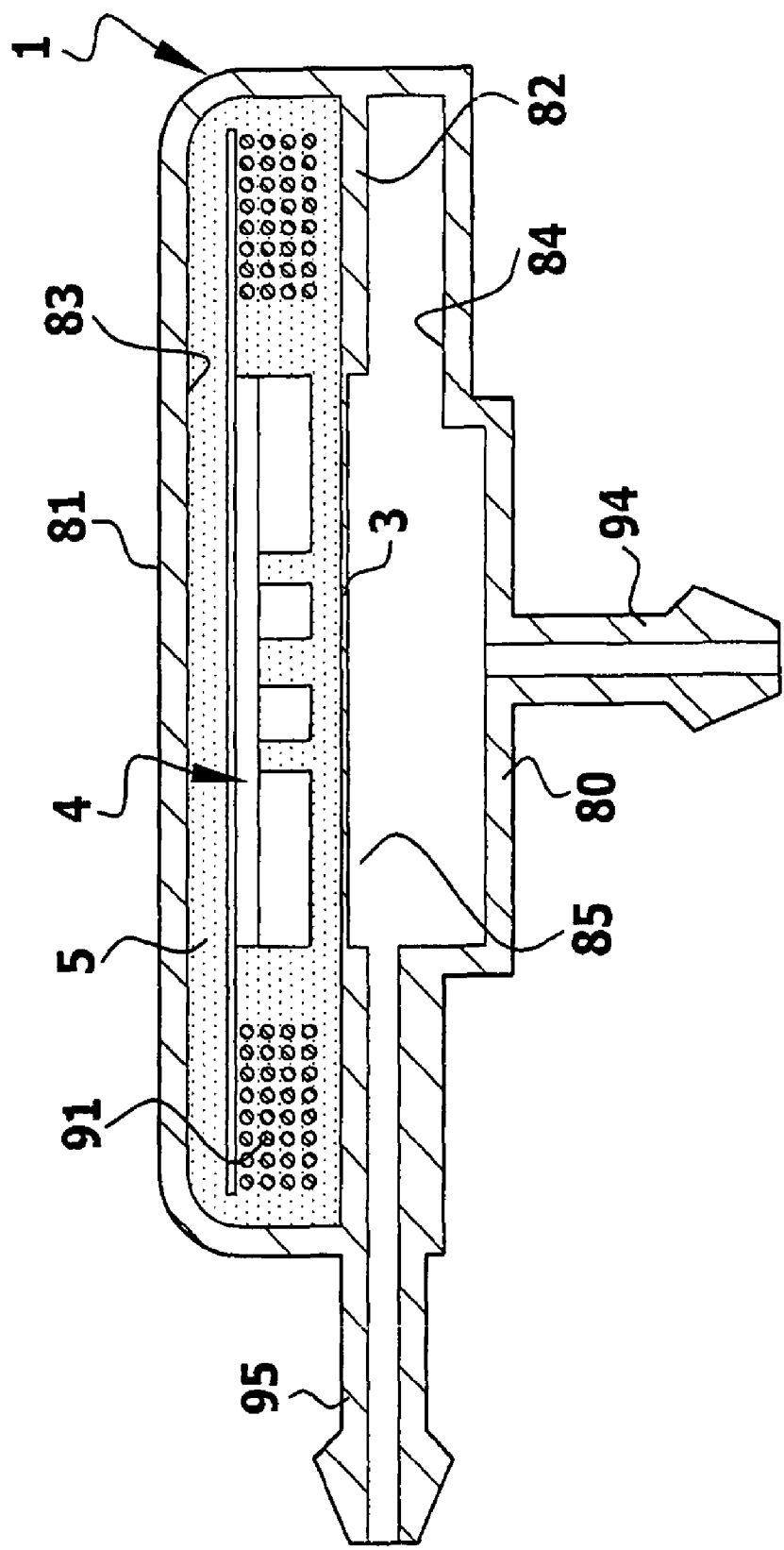
FIG. 23 is a view similar to FIG. 22 with a supply conduit opening vertically into the floor of the housing.
Figure 24:
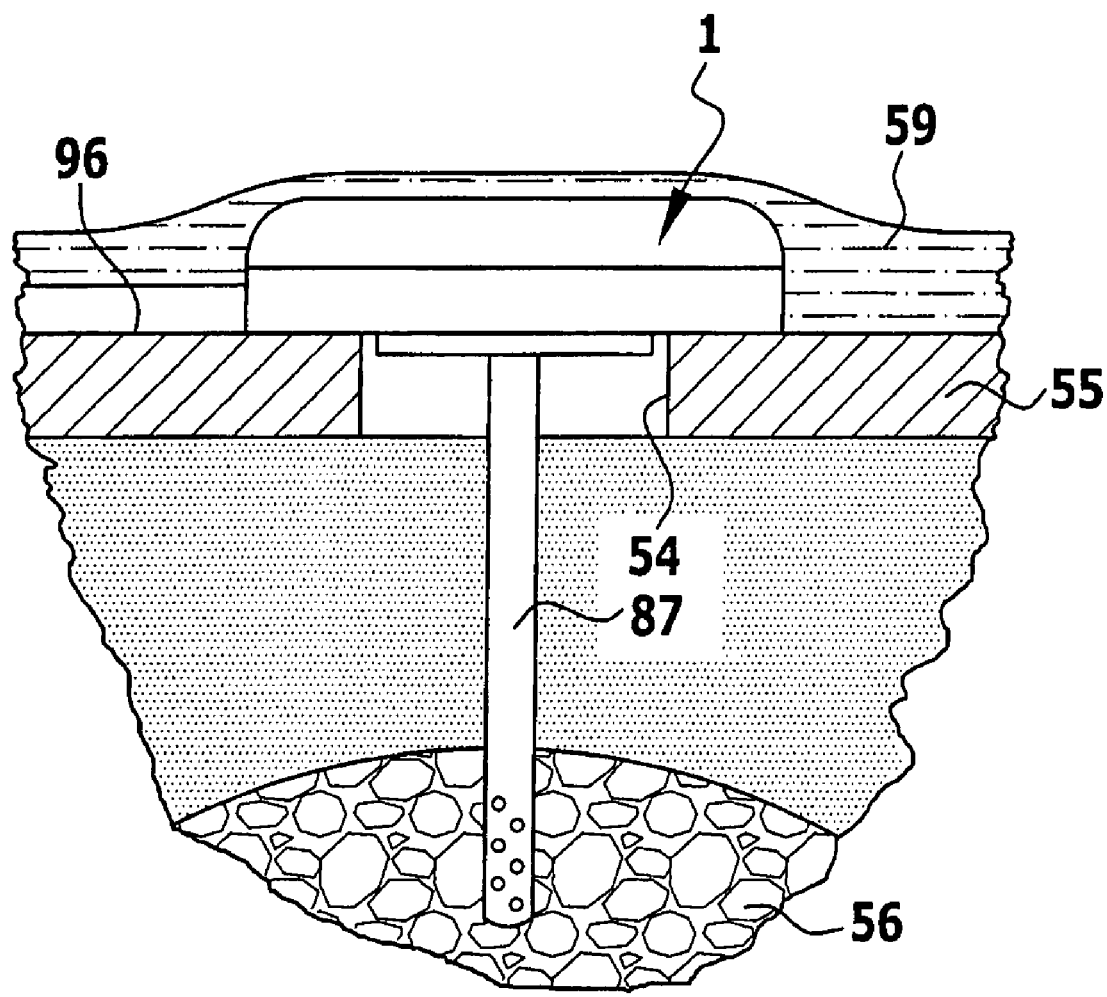
FIG. 24 is a schematic representation of a rigid housing covering a drill hole in the top of the cranium with a catheter-type supply conduit.

In the exemplary embodiment of FIG. 22 both pipe connections 94 and 95 run parallel to the floor surface, but arrangements such as shown in FIG. 23 are also possible. In this case, a pipe connection 94 flows from below vertically to the floor surface 80 centrally into the fluid chamber 84, whereas the second pipe connection 95 exits laterally parallel to the floor surface. Such a device is used in the manner described in FIG. 24, so that the tube 87 projects through the drill hole 54 in the top of the cranium 55 into the interior of the cranium, in which case the housing 1 covers the drill hole 54. The housing 1 is arranged between the top of the cranium 55 and the scalp 59, a drainage pipe 96 can run directly on the top of the cranium 55 and under the scalp 59.

Figure 25:
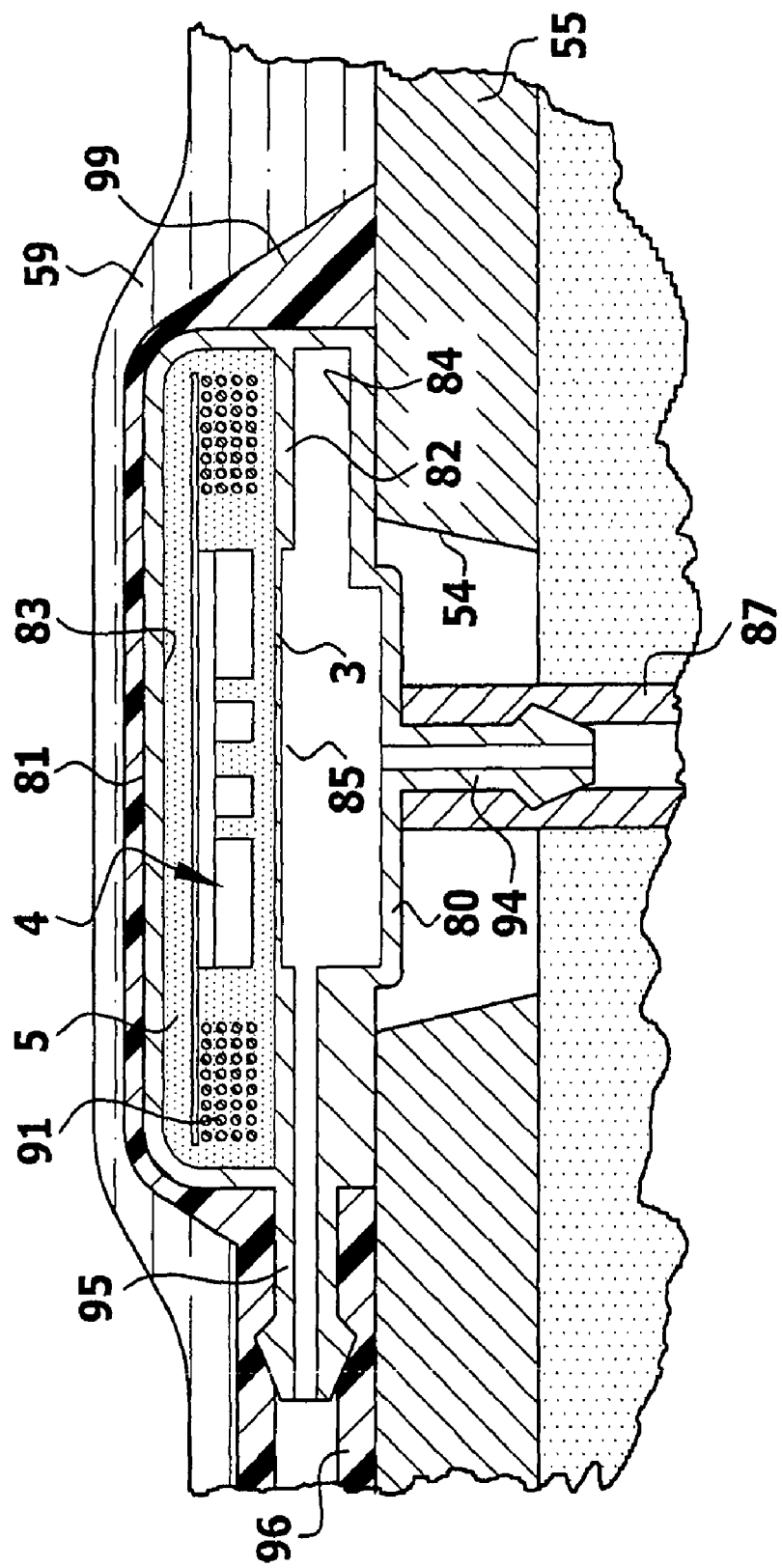
FIG. 25 is a view similar to FIG. 23 with a protective cap covering the rigid housing.
Figure 26:
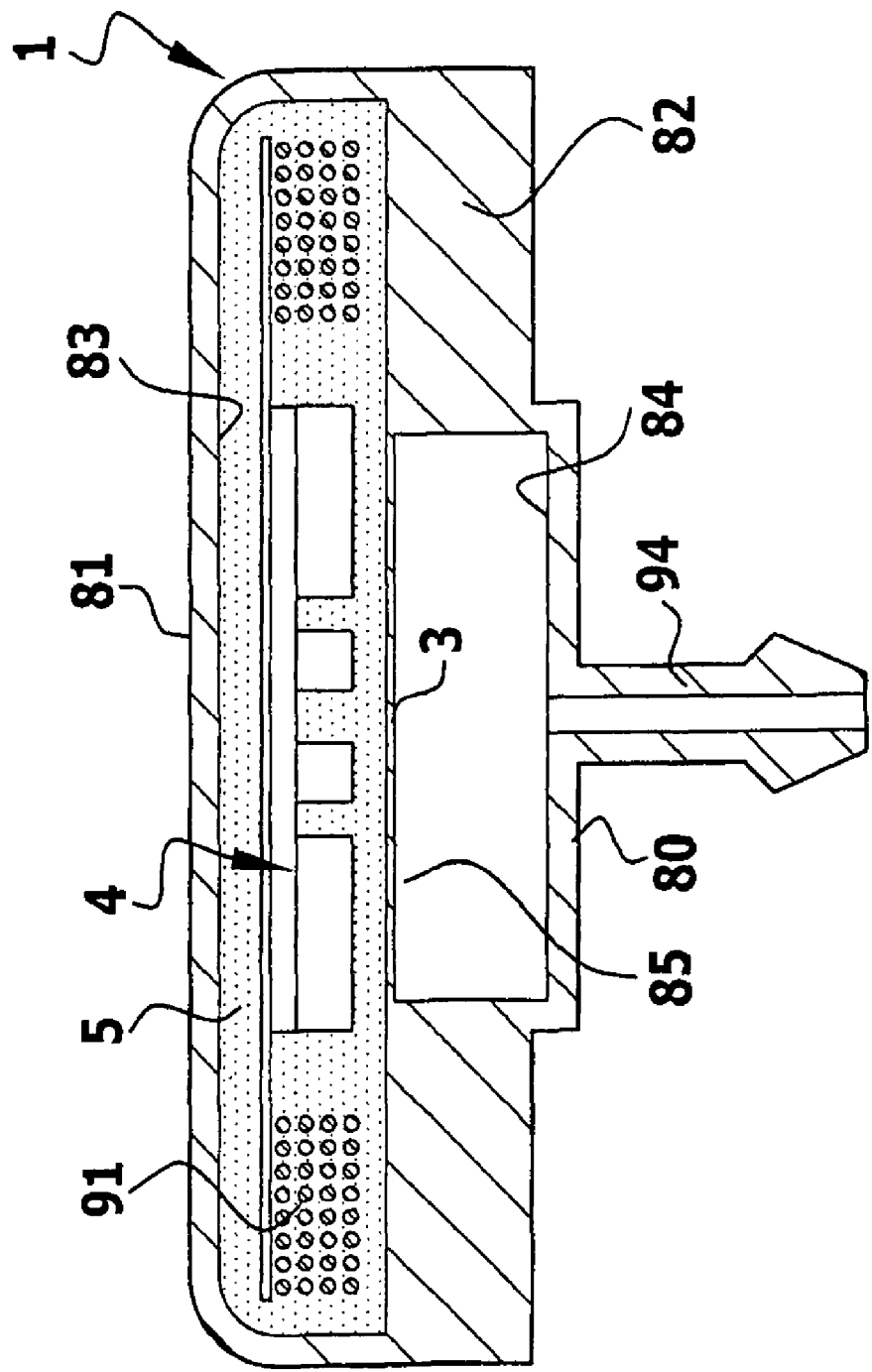
FIG. 26 is a view of a rigid housing similar to FIG. 23, but without a drainage pipe.

A similar arrangement is described in FIG. 25, wherein a protective cap 99 additionally engages over the housing 1, so that both the housing 1 and the surrounding tissue are additionally protected.

If a vulcanised or polymerised material, in particular a cross-linked silicone, is used as transfer medium inside the housing 1, then the entire cavity between the microchip 4 and the membrane 3 can be filled with this material, so that a pressure transfer then occurs over the full surface.

However, it is also possible that the pressure transfer occurs only in a sub-region of the microchip.

Figure 35A:
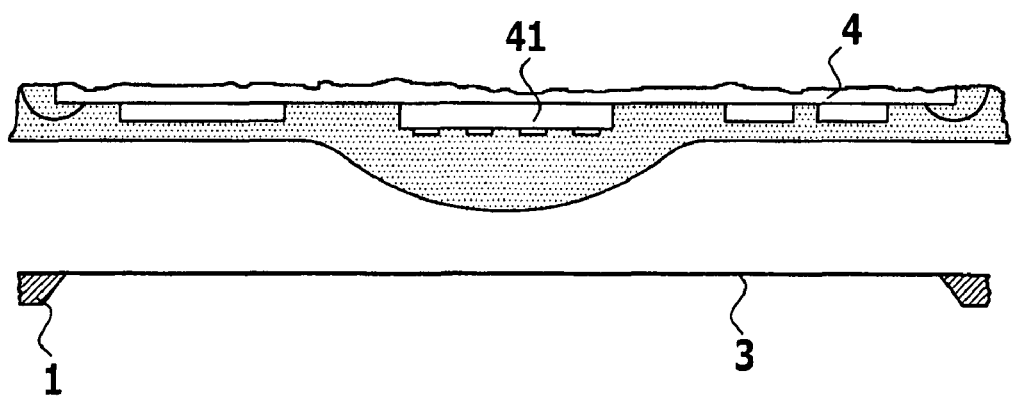
FIG. 35*a* is a schematic representation of a sub-region of the microchip with a silicone coating before the final positioning of the microchip and membrane.
Figure 35B:
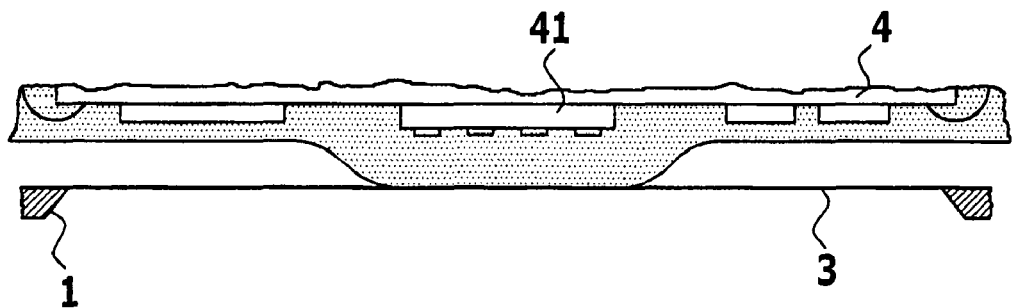
FIG. 35*b* is a view similar to FIG. 35*a* after the final positioning of the microchip and membrane with the silicone coating abutting against the membrane in sections.

In the exemplary embodiment of FIG. 35a it is shown that the microchip is covered over the full surface by such a vulcanised or polymerised material, hereafter abbreviated to transfer material, but that this transfer material has a greater thickness in the region of the pressure sensor 41. In the installed state, the microchip 4 and the membrane 3 lie so close together that in this central region, in which the transfer material has a greater thickness, this material abuts against the membrane 3, as is shown in FIG. 35b, so that a pressure transfer occurs in this region. This pressure transfer is therefore concentrated onto the region of the pressure sensor 41.

Figure 36A:
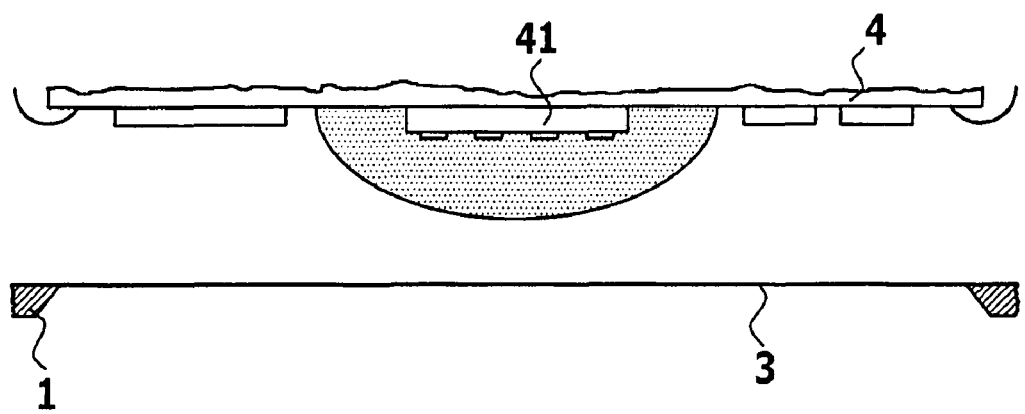
FIG. 36*a* is a view similar to FIG. 35*a* with the microchip only coated in sections.
Figure 36B:
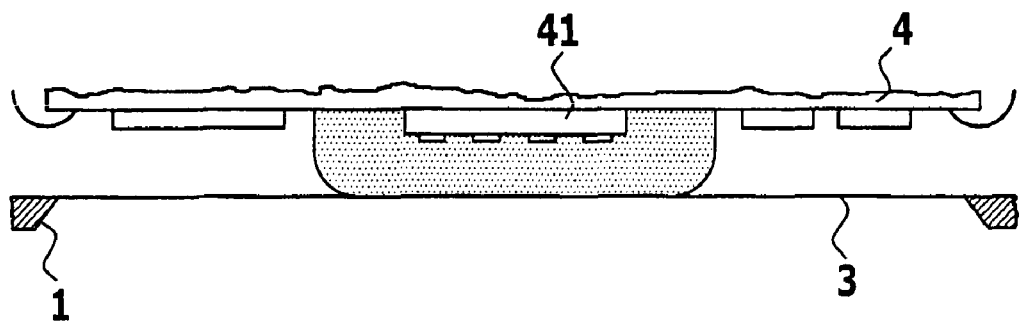
FIG. 36*b* is a view similar to FIG. 35*b* with the microchip only coated in sections.
Figure 37A:
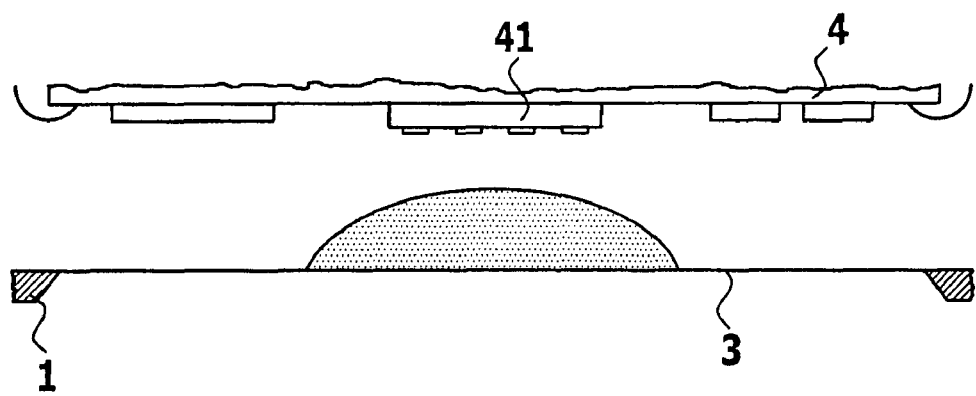
FIG. 37*a* is a view similar to FIG. 35*a* with a silicone coating on the membrane.
Figure 37B:
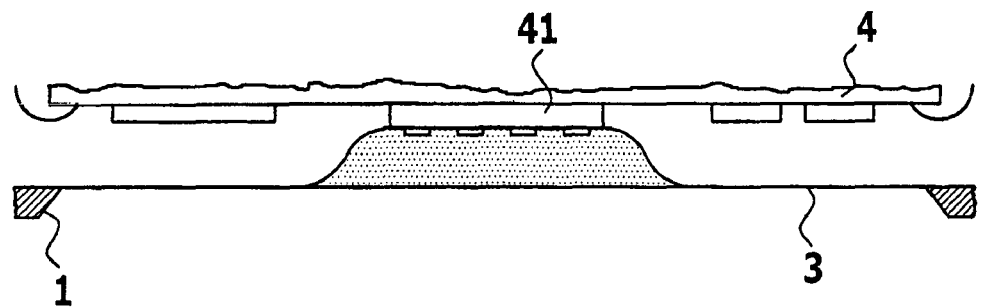
FIG. 37*b* is a view similar to FIG. 35*b* with a silicone coating on the membrane.

It is also possible that according to the configuration of FIGS. 36a and 36b only the region of the pressure sensor 41 is encased by the transfer material, whereas externally located edge regions of the microchip remain free of the transfer material.

Finally, it is possible that the microchip is not coated at all with the transfer material, instead the transfer material is arranged on the membrane 3, so that a pressure-transferring layer of the transfer material is formed between the membrane 3 and the pressure sensor 41 as a result.

Figure 38:
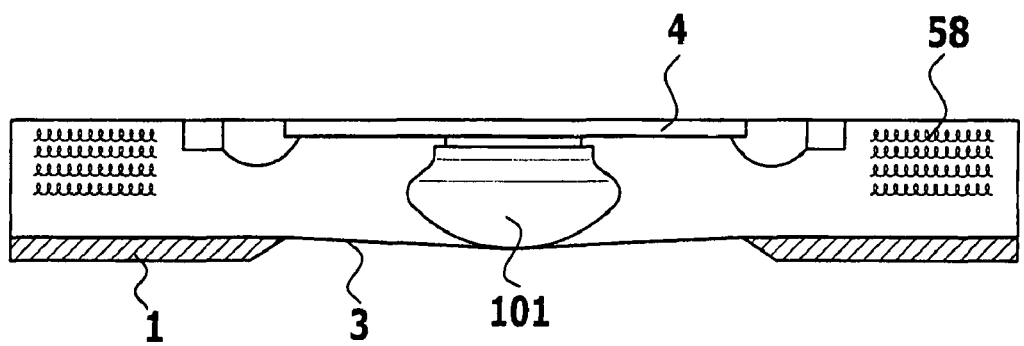
FIG. 38 is a schematic side view of a housing with a membrane and a pressure foot held on the microchip and supported on the membrane.
Figure 39:
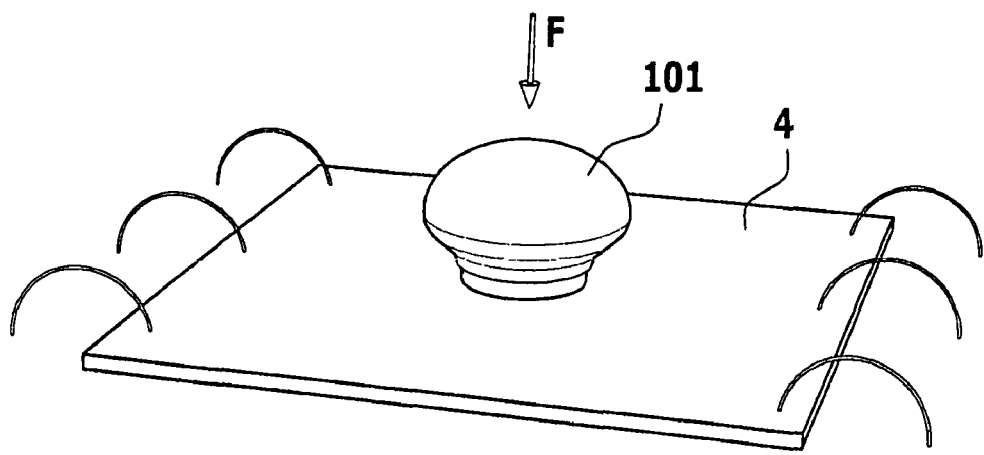
FIG. 39 is a schematic perspective view of the arrangement of the microchip and pressure foot according to FIG. 38.

Finally, it is also possible in a modified exemplary embodiment to conduct the pressure transfer by means of mechanical pressure transfer elements, e.g. by a pressure foot 101, which is disposed on the microchip 4 and is supported against the membrane 3, as is shown in FIGS. 38 and 39. This pressure foot 101 then transfers the pressure forces from the membrane 3 to the pressure sensor 41.

Figure 40:
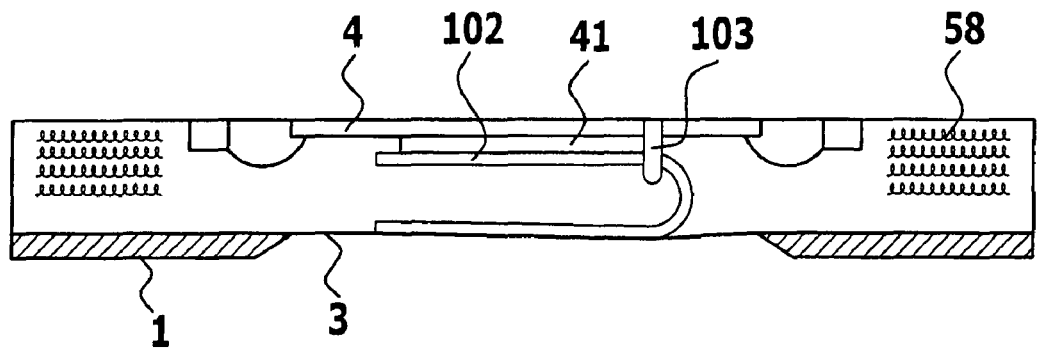
FIG. 40 is a schematic sectional view through a housing with the membrane and a U-shaped clip-type spring between the microchip and membrane.
Figure 41:
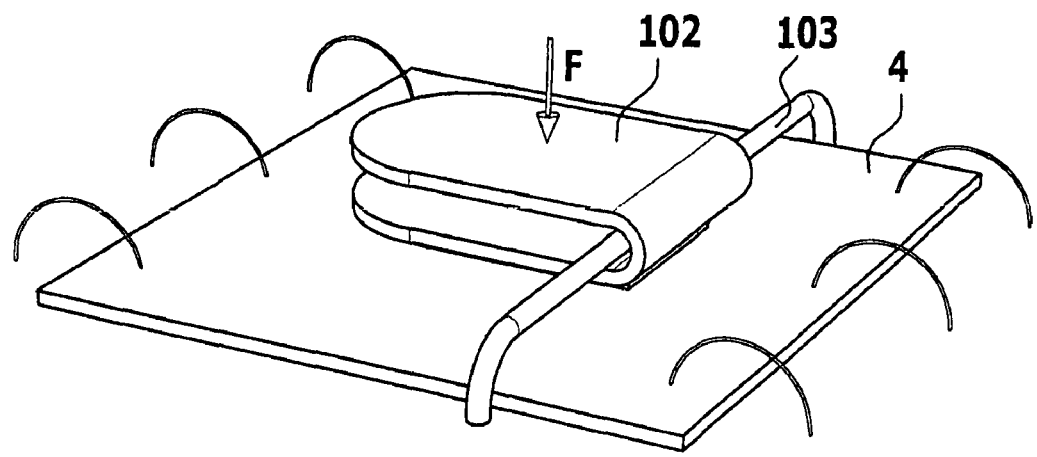
FIG. 41 is a schematic view of the arrangement of the microchip and leaf spring according to FIG. 40.

A spring element, e.g. a U-shaped leaf spring 102, which is supported against the pressure sensor 41 on one side and against the membrane 3 on the other, as is shown in FIGS. 40 and 41, can also be inserted between the microchip 4 and the membrane 3 in place of the pressure foot 101. Such a leaf-spring 102 can be disposed on the housing 1 or on a support 37 holding the microchip 4 by means of lateral crosspieces 103.

Figure 42:
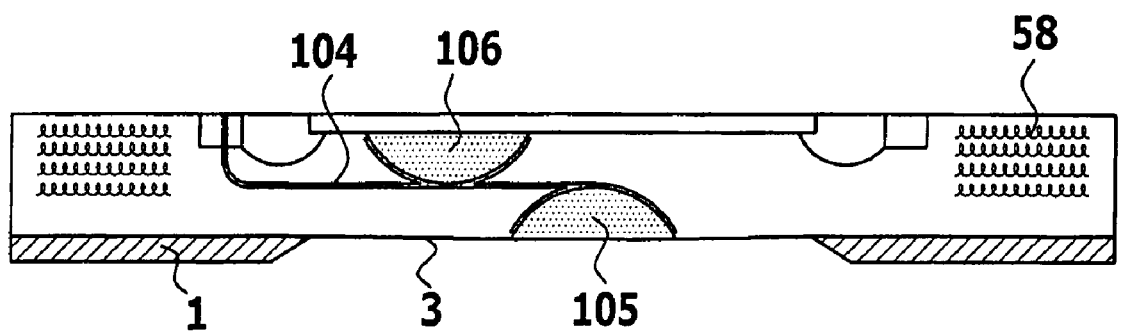
FIG. 42 is a view similar to FIG. 40 in the case of an exemplary embodiment with a clip and two pressure feet.

FIG. 42 shows a modified design for a mechanical pressure transfer element, namely a clip 104, which is disposed on the housing 1 or a support 37, and which is supported on the membrane 3 by means of a first foot 105 and on the pressure sensor 41 by means of a second foot 106 and in this way transfers the pressure forces from the membrane 3 to the pressure sensor 41.

Figure 43:
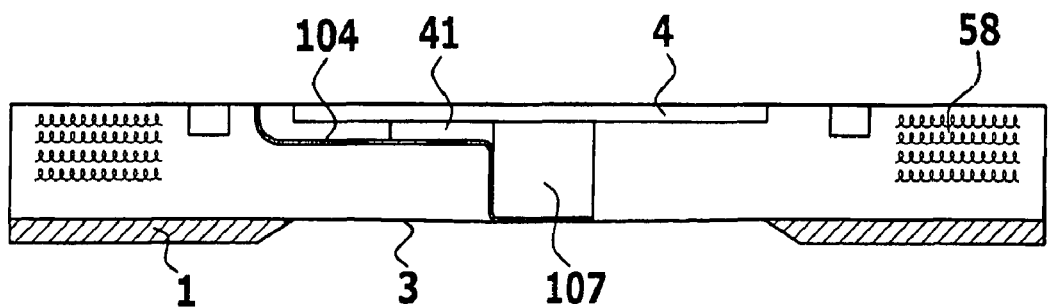
FIG. 43 is a view similar to F*igure* 40 with a clip having a lateral crosspiece.
Figure 44:
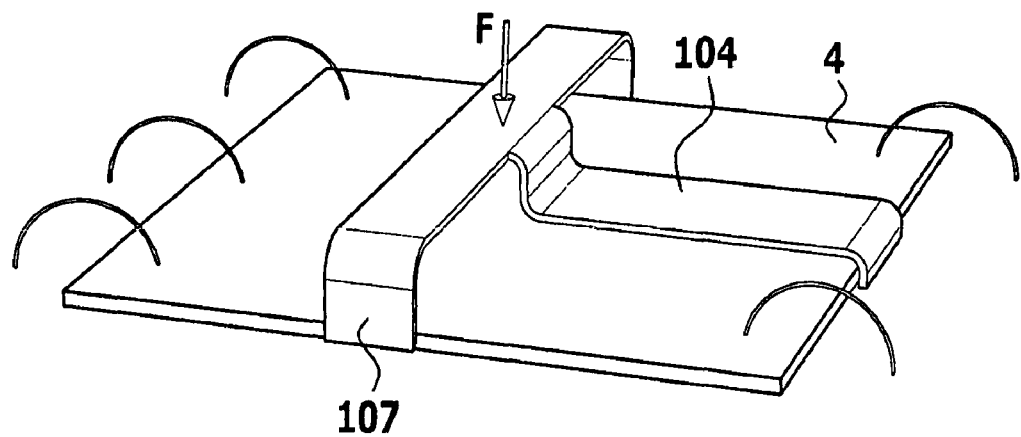
FIG. 44 is a view of the arrangement comprising microchip and clip according to FIG. 43.

As may be seen from FIGS. 43 and 44, such a clip 104 can bear lateral crosspieces 107, which act as a stop and which restrict movement of the clip 104 to thus prevent overload and damage to the entire arrangement. Such stops can be provided in all arrangements that transfer the pressure forces mechanically to the pressure sensor 41.

Figure 45:
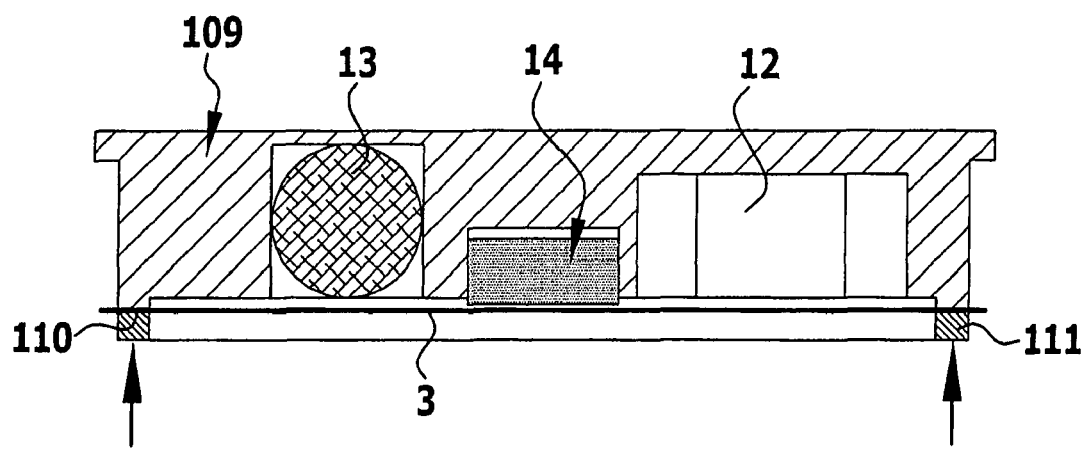
FIG. 45 is a sectional view through an insert receiving a measurement chamber with a membrane closing off the measurement chamber.
Figure 46:
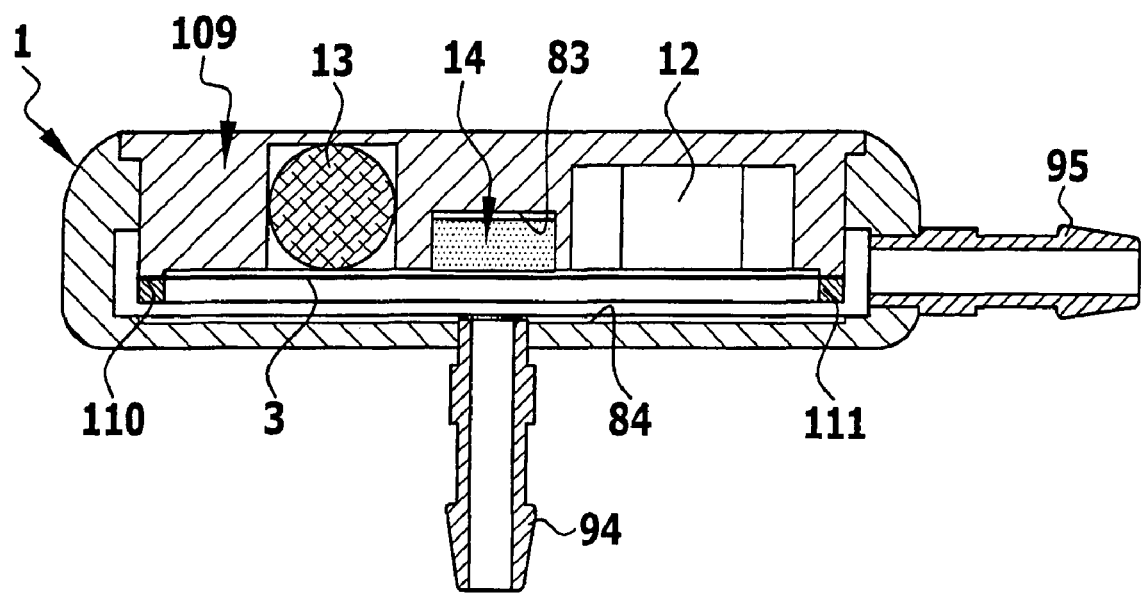
FIG. 46 is a sectional view through a housing with an insert inserted into the housing according to FIG. 45.

A further possible configuration for a rigid housing 2 is shown in FIGS. 44 and 45. In this case, as in the exemplary embodiment of FIG. 23, the rigid housing 2 is provided with a pipe connection 94 that opens centrally and vertically therein from below and with a pipe connection 95 that exits horizontally and radially and is open at the upper side. An insert 109, which tightly closes the housing 2 on the upper side, is inserted into the upper side that is open at the top. The insert 109 receives the microchip 14 as well as electronic unit 12 and electronic unit 13 in a similar manner to the transfer medium 5 in the exemplary embodiment of FIG. 5. On its underside the insert 109 has a plane circumferential edge 110, which runs along its outer contour and projects downwards beyond it only very slightly. The plane membrane 3 configured as a thin metal foil is laid flat against this planar rim 110 and is clamped between the insert 109 on one side and an annular abutment element 111 on the other side, which lies opposite the edge 110 and terminates with this on the outside.

The insert 109 and the membrane 3 are soldered or welded together in the region of the abutment element 111 and the edge 110.

To create this connection, the membrane 3 is firstly arranged to abut flat against the edge 110 before being inserted into the housing 2 and is pressed against the edge 110 by means of the abutment element 111, i.e. by means of a contact pressure K (FIG. 45). In this case the dimension of the membrane is selected so that this projects laterally slightly beyond the insert 109 and the abutment element 111, as is clear from FIG. 45. The soldering or welding to the insert 109 and the abutment element 111 occurs in this region of the slightly projecting edge of the membrane 3. In particular, in the case of a welding process the projecting edge region of the membrane can be removed during the welding, so that a flush closure of the membrane 3 with the insert 109 and the abutment element 111 can be achieved.

This structural unit with the welded or soldered membrane 3 is then inserted into the upwardly open housing 2 and seals this as a result. The still unoccupied interior of the housing 2 then forms the fluid chamber 84, through which the brain fluid flows, the pressure of which is to be determined.

What is claimed is:

1. Implantable device for determining intracranial pressures, comprising:
   a rigid housing defining a housing interior;
   a thin biocompatible membrane closing off at least a portion of the housing interior; and
   a pressure measuring device arranged in the housing interior, the pressure measuring device being a microchip which comprises a pressure sensor for determining a value of a pressure transfer occurring through the membrane from an outside of the membrane inwards towards the housing interior, wherein:
   the value of the pressure transfer is telemetrically communicated via the pressure measuring device;
   a pressure-dependent movement of the membrane acts on the pressure measuring device via a transfer medium,
   the transfer medium comprises one of air or a special gas,
   the housing interior is filled with a gas-displacing filler material except for a provided volume of the transfer medium,
   the rigid housing has a closed fluid chamber which adjoins the membrane on the outside of the membrane and is connected to a supply conduit for fluid,
   the rigid housing has the shape of a shallow can with an upper measurement chamber receiving the microchip and the transfer medium and a lower region forming the fluid chamber,
   the membrane divides the housing interior into the measurement chamber and the fluid chamber,
   the supply conduit for fluid runs substantially perpendicular in relation to a lower boundary wall of the fluid chamber.

2. Device according to claim 1, wherein the transfer medium comprises a gas from the group of noble gases.

3. Device according to claim 1, wherein:
   a gas is used as transfer medium, and
   a gas volume of the gas is less than a cubic millimetre.

4. Device according to claim 1, wherein the filler material is one of plastic, ceramic or a metal material.

5. Device according to claim 1, wherein:
   the filler material forms a minimum-volume pressure chamber including a supply duct on pressure-sensitive faces of the microchip,
   the filler material forms a housing cavity as pressure chamber below the membrane, and
   the two pressure chambers are connected by a small-volume conduit.

6. Device according to claim 1, wherein the housing is made of ceramic.

7. Device according to claim 1, wherein the housing is made of a biocompatible plastic.

8. Device according to claim 7, wherein the housing is made of one of polyether ether ketone or polyether ketone ketone.

9. Device according to claim 1, wherein the housing is made of metal.

10. Device according to claim 9, wherein the housing is made of one of titanium or a titanium alloy.

11. Device according to claim 1, wherein the membrane is made of metal.

12. Device according to claim 11, wherein the membrane is made of one of titanium or a titanium alloy.

13. Device according to claim 1, wherein the membrane has a thickness of less than 0.05 millimetres.

14. Device according to claim 1, wherein the membrane has a flexible surface of about one of 100 mm$^2$, 1 mm$^2$, and 4 mm$^2$.

15. Device according to claim 1, wherein the membrane is welded to the housing.

16. Device according to claim 15, wherein the membrane is provided with a sheet metal frame and is welded with the frame to the housing.

17. Device according to claim 1, wherein the membrane is configured in one piece with the housing.

18. Device according to claim 1, wherein the membrane has regions of different thickness.

19. Device according to claim 18, wherein the membrane is thicker in its edge regions than in its central region.

20. Device according to claim 1, wherein besides the pressure sensor, the microchip comprises at least one further sensor.

21. Device according to claim 20, wherein the microchip further comprises an analog-to-digital converter, which converts the analog electrical signals of the sensors into digital signals.

22. Device according to claim 1, the microchip is arranged on a support.

23. Device according to claim 22, wherein the support is bend-resistant.

24. Device according to claim 22, wherein the support carries further electronic components.

25. Device according to claim 24, wherein the support has connection leads for at least one of the microchip and the further electronic components.

26. Device according to claim 22, wherein the microchip or the support is connected to a power and signal transmission line, which line connects to a data processing device outside a body or to a transmission coil.

27. Device according to claim 26, wherein the transmission coil is arranged in the rigid housing.

28. Device according to claim 1, wherein the rigid housing is partially provided with a plastic casing or a plastic covering, which leaves at the least the surface of the membrane free.

29. Device according to claim 1, wherein the fluid chamber additionally has a drainage pipe for brain fluid.

30. Device according to claim 1, wherein the supply conduit for fluid enters the fluid chamber approximately centrally.

31. Device according to claim 29, wherein the drainage pipe for the brain fluid runs parallel to a floor surface of the fluid chamber.

32. Device according to claim 29, wherein a non-return valve is arranged in the drainage pipe.

33. Device according to claim 29, wherein the drainage pipe opens into a reservoir.

34. Device according to claim 1, wherein the supply conduit is connected to an extension tube, which is open at its end remote from the fluid chamber.

35. Device according to claim 1, wherein:
the supply conduit is connected to an extension tube, which is closed at its end remote from the fluid chamber by means of a flexible membrane, and
the fluid chamber filled with a liquid or a gas is closed off except for the supply conduit.

36. Device according to claim 1, wherein a wall thickness of the rigid housing lies between 0.3 mm and 0.2 mm.

37. Device according to claim 1, wherein walls of the rigid housing are protected against deformation by reinforcement structures.

38. Device according to claim 1, wherein:
the measurement chamber is arranged in an insert, which can be inserted into the housing and closes the housing in the manner of a cover, and
the insert carries the membrane, which separates the measurement chamber from the fluid chamber.

39. Device according to claim 38, wherein the membrane is a metal foil, which is soldered or welded to the insert receiving the measurement chamber.

40. Device according to claim 39, wherein:
the insert receiving the measurement chamber has a planar rim, against which the membrane lies flat,
an annular abutment element is arranged opposite the planar rim on the side opposite the insert, and
the membrane is soldered or welded both to the insert and to the abutment element.

41. Device according to claim 39, wherein, the element is made of metal.

42. Device according to claim 40, wherein the abutment element is made of metal.

43. Device according to claim 39, wherein the membrane is made of metal.

44. Device according to claim 43, wherein the thickness of the membrane lies between $1/100$ mm and $5/100$ mm.

45. Device according to claim 40, wherein the abutment element has a height of between $2/10$ and $8/10$ mm.

* * * * *